US009993655B2

United States Patent
Saitoh et al.

(10) Patent No.: US 9,993,655 B2
(45) Date of Patent: Jun. 12, 2018

(54) IMAGE DATA PROCESSING DEVICE AND TRANSCRANIAL MAGNETIC STIMULATION APPARATUS

(75) Inventors: Youichi Saitoh, Suita (JP); Kuniyoshi Uchida, Suita (JP); Koichi Hosomi, Suita (JP); Yoshihiro Yasumuro, Suita (JP); Tatsuya Ogino, Suita (JP)

(73) Assignees: OSAKA UNIVERSITY, Suita-shi, Osaka (JP); A SCHOOL CORPORATION KANSAI UNIVERSITY, Suita-shi, Osaka (JP)

( * ) Notice: Subject to any disclaimer, the term of this patent is extended or adjusted under 35 U.S.C. 154(b) by 0 days. days.

(21) Appl. No.: 14/004,060

(22) PCT Filed: Mar. 8, 2012

(86) PCT No.: PCT/JP2012/055995
§ 371 (c)(1),
(2), (4) Date: Sep. 9, 2013

(87) PCT Pub. No.: WO2012/121341
PCT Pub. Date: Sep. 13, 2012

(65) Prior Publication Data
US 2013/0345491 A1    Dec. 26, 2013

(30) Foreign Application Priority Data

Mar. 9, 2011    (JP) .................... 2011-051871

(51) Int. Cl.
*G06K 9/00* (2006.01)
*A61N 2/00* (2006.01)
(Continued)

(52) U.S. Cl.
CPC .............. *A61N 2/00* (2013.01); *A61B 5/0042* (2013.01); *A61B 5/055* (2013.01); *A61B 5/1114* (2013.01);
(Continued)

(58) Field of Classification Search
CPC .......... A61N 2/02; A61N 2/008; A61B 5/061; G06Q 10/087
See application file for complete search history.

(56) References Cited

U.S. PATENT DOCUMENTS 5,999,840 A    12/1999 Grimson et al.
6,072,903 A    6/2000 Maki et al.
(Continued)

FOREIGN PATENT DOCUMENTS

JP    9-511430 A    11/1997
JP    2003-180649 A    7/2003
(Continued)

OTHER PUBLICATIONS

Noirhomme et al., Registration and Real-Time Visualization of Transcranial Magnetic Stimulation With 3-D MR Images, IEEE Transactions on Biomedical Engineering, vol. 51, No. 11, 2004, pp. 1994-2005.*
(Continued)

*Primary Examiner* — Vu Le
*Assistant Examiner* — Guillermo Rivera-Martinez
(74) *Attorney, Agent, or Firm* — Sughrue Mion, PLLC

(57) ABSTRACT

An image data processing device including: a storage means configured to store a three-dimensional MRI image of a subject's head; a three-dimensional appearance image generation means configured to generate a three-dimensional appearance image of the head; an image generation means configured to perform positional alignment between the three-dimensional MRI image and the three-dimensional appearance image, and to generate a three-dimensional image of the head after the positional alignment; an after-movement image generation means configured to generate, when the subject's head has been moved, a three-dimensional subject's head image after the movement and the
(Continued)

(a) BEFORE POSITIONAL ALIGNMENT (b) AFTER POSITIONAL ALIGNMENT positional alignment; an operational object image generation means configured to generate an operational object image indicating a position of an operational object; and a display means configured to display the three-dimensional image of the subject's head after the movement and the operational object image in one image.

22 Claims, 21 Drawing Sheets

(51) Int. Cl.
| | |
|---|---|
| A61B 5/00 | (2006.01) |
| A61B 5/055 | (2006.01) |
| A61B 5/11 | (2006.01) |
| G06T 11/00 | (2006.01) |
| G06T 7/33 | (2017.01) |
| G06T 7/593 | (2017.01) |
| G06T 7/246 | (2017.01) |
| A61N 2/02 | (2006.01) |
| A61B 5/06 | (2006.01) |

(52) U.S. Cl.
CPC .......... *A61B 5/1128* (2013.01); *A61B 5/7425* (2013.01); *A61N 2/006* (2013.01); *G06T 7/251* (2017.01); *G06T 7/344* (2017.01); *G06T 7/593* (2017.01); *G06T 11/008* (2013.01); *A61B 5/061* (2013.01); *A61B 5/7207* (2013.01); *A61N 2/02* (2013.01); *G06T 2207/10028* (2013.01); *G06T 2207/10088* (2013.01); *G06T 2207/30016* (2013.01); *G06T 2207/30201* (2013.01)

(56) References Cited

U.S. PATENT DOCUMENTS

| | | | |
|---|---|---|---|
| 2003/0050527 A1 | 3/2003 | Fox et al. | |
| 2003/0073899 A1 | 4/2003 | Ruohonen et al. | |
| 2004/0039279 A1 | 2/2004 | Ruohonen | |
| 2005/0033380 A1 | 2/2005 | Tanner et al. | |
| 2005/0113630 A1* | 5/2005 | Fox et al. | 600/13 |
| 2007/0238981 A1 | 10/2007 | Zhu et al. | |
| 2008/0064950 A1* | 3/2008 | Ruohonen et al. | 600/411 |
| 2008/0269588 A1 | 10/2008 | Csavoy et al. | |
| 2009/0177081 A1 | 7/2009 | Joskowicz et al. | |
| 2009/0187062 A1* | 7/2009 | Saitoh | 600/13 |
| 2010/0172567 A1* | 7/2010 | Prokoski | A61B 5/0064 382/132 |
| 2011/0054300 A1 | 3/2011 | Yamamoto et al. | |
| 2012/0114208 A1 | 5/2012 | Hirasawa et al. | |
| 2013/0178693 A1* | 7/2013 | Neuvonen et al. | 600/13 |
| 2014/0235929 A1* | 8/2014 | Rohan | 600/14 |

FOREIGN PATENT DOCUMENTS

| | | |
|---|---|---|
| JP | 2004-636 A | 1/2004 |
| JP | 2006-320425 A | 11/2006 |
| JP | 2007-209531 A | 8/2007 |
| JP | 2008-526422 A | 7/2008 |
| JP | 2008-262555 A | 10/2008 |
| JP | 2009-529951 A | 8/2009 |
| WO | 96/07144 A1 | 3/1996 |
| WO | 2006/075331 A2 | 7/2006 |
| WO | 2007/106046 A2 | 9/2007 |
| WO | 2007/123147 A1 | 11/2007 |
| WO | 2008/031847 | 3/2008 |
| WO | 2010/143400 A1 | 12/2010 |

OTHER PUBLICATIONS

Koessler et al., EEG-MRI Co-registration and Sensor Labeling Using a 3D Laser Scanner, Annals of Biomedical Engineering, vol. 39, No. 3, Mar. 2011, pp. 983-995.*

Maurer at al., Registration of 3-D Images Using Wighted Geometrical Features, 1996, Ransactions on Medical Imaging, vol. 15, No. 6, pp. 836-849.*

Translation of International Preliminary Report on Patentability dated Sep. 19, 2013 for International Application No. PCT/JP2012/055995.

Paul J. Besl et al. "A Method for Registration of 3-D Shapes", IEEE Transations on Pattern Analysis and Machine Intelligence, Feb. 1992, pp. 239-256, vol. 14, No. 2.

Masayuki Hirata et al., "Preoperative and intraoperative evaluation of visual function using magnetoencephalography, electrocorticogram, fiber tracking and transcranial magnetic stimulation", Rinsho Noha, Dec. 2009, pp. 721-728, vol. 51, No. 12.

International Search Report for PCT/JP2012/055995 dated Jun. 12, 2012.

Extended European Search Report for European Patent Application 12754418.7 dated Aug. 21, 2014.

Extended European Search Report for European Patent Application 15159364.7 dated Aug. 17, 2015.

Japanese Office Action (Notification of Reasons for Refusal) dated Nov. 1, 2016, in Japanese application 2013-503607.

Matsumoto et al., "Development of Face and Gaze Measurement System and Its Application to Interfaces" IEICE Technical Report, dated Feb. 23, 2007.

* cited by examiner

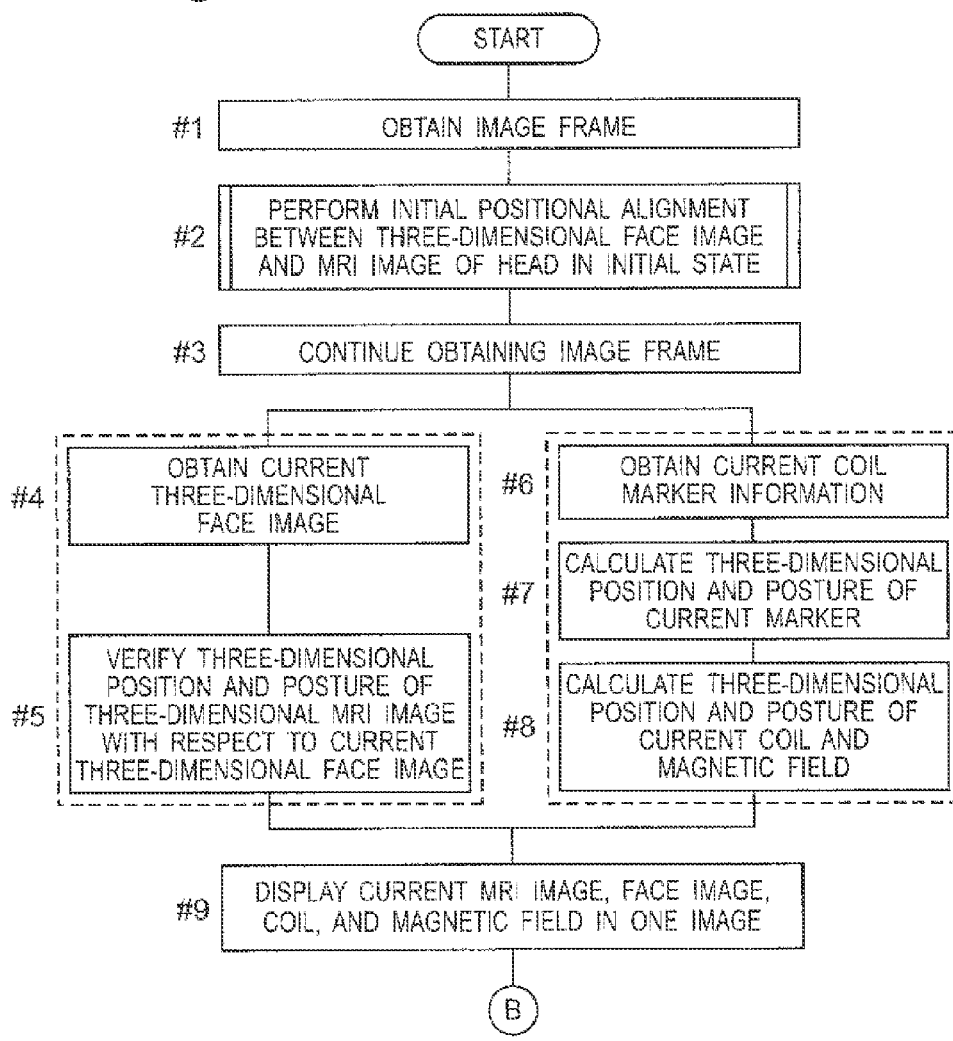

<POINT GROUP AND DISTANCE>

<CORRESPONDENCE POINTS IN ICP ALGORITHM>

<PARALLELIZATION OF BLOCK MATCHING>

<THREE-DIMENSIONAL DISPLAY OF MARKER AND STIMULATION TARGET SITE>

(a) <MRI TRANSVERSE CROSS-SECTIONAL IMAGE>
(b) <EXTRACTION OF BRAIN REGION>
(c) <THREE-DIMENSIONAL DISPLAY (POINT GROUP)>

Fig.16
(a) 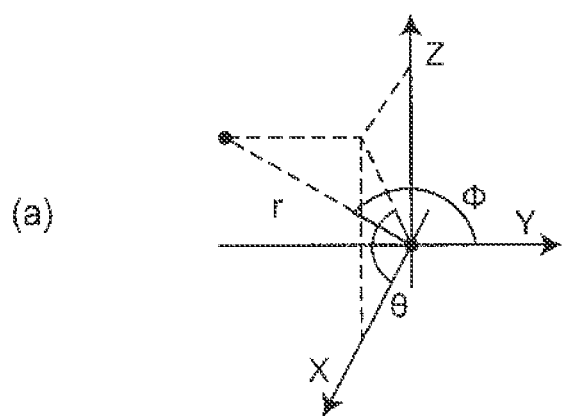
<POLAR COORDINATES>
(b) 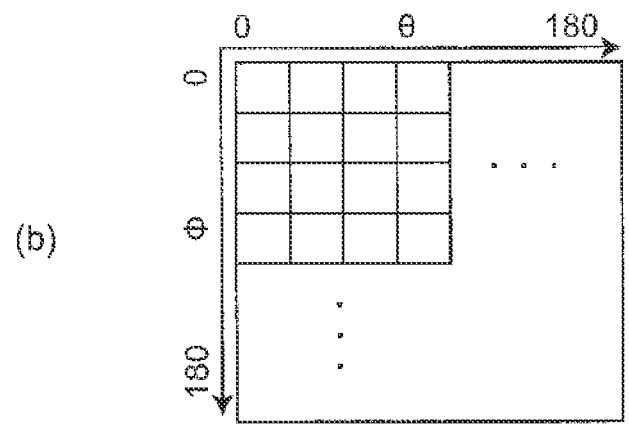
<ARRAY FOR STORING COLOR INFORMATION>

<TEXTURE IMAGE>

IMAGE DATA PROCESSING DEVICE AND TRANSCRANIAL MAGNETIC STIMULATION APPARATUS

CROSS REFERENCE TO RELATED APPLICATIONS

This application is a National Stage of International Application No. PCT/JP2012/055995 filed Mar. 8, 2012, claiming priority based on Japanese Patent Application No. 2011-051871 filed Mar. 9, 2011, the contents of all of which are incorporated herein by reference in their entirety.

TECHNICAL FIELD

The present invention relates to an image data processing device, and a transcranial magnetic stimulation apparatus utilizing such the image data processing device.

BACKGROUND ART

In recent years, a transcranial magnetic stimulation treatment is increasingly receiving attentions as a treatment method to patients of various neural diseases for which medication is not always effective. The transcranial magnetic stimulation treatment is a relatively new treatment method for applying magnetic stimulation to a particular region of the brain (brain nerve, for example) by a magnetic field generating source provided on the surface of a patient's scalp, thereby capable of providing a treatment and/or relieving symptoms. Unlike the conventional electric stimulation requiring a craniotomy procedure and using an implanted electrode that makes a patient highly uncomfortable, the transcranial magnetic stimulation treatment is expected to be broadly used as a treatment method that is non-invasive and less stressful for patients.

As a specific method of such a transcranial magnetic stimulation treatment, there is known a method of applying electrical current to a coil positioned near the surface of a patient's scalp, regionally generating a small pulsed magnetic field, generating eddy current within a cranium based on a principle of electromagnetic induction, and applying stimulation to the brain nerve immediately under the coil (see Patent Literature 1, for example).

According to Patent Literature 1, it is confirmed that the transcranial magnetic stimulation treatment provided according to the above method effectively relieves intractable neuropathic pains, and in addition, provides a higher effect for pain relief by applying focal stimulation more accurately. However, it is also disclosed that optimum stimulating portions of individual patients are delicately different.

Therefore, in order to achieve a higher effect with the transcranial magnetic stimulation treatment, it is important how an optimum stimulating portion on a patient's head is determined for each patient, or more specifically, how three-dimensional positioning of a treatment coil to the patient's head is performed accurately. It should be noted that it is also known that even if the position of the treatment coil is the same, an achieved effect varies depending on an orientation (posture) of the coil.

Known configurations of the positioning of such a treatment coil include positioning of a treatment coil on the patient's head utilizing an optical tracking system using infrared rays (see Patent Literatures 2 and 3, for example), and some are commercially available and applied in clinical settings.

As described above, in order to achieve an effect for pain relief with the transcranial magnetic stimulation treatment, it is necessary to specify an optimum stimulating portion on a patient's head and accurately apply stimulation to the brain nerve at the portion. While it is difficult to grasp an accurate position of the brain within the cranium from outside, it is possible to grasp its position accurately using three-dimensional information of an MRI (Magnetic Resonance Imaging) image of the head. By using a positioning function of the optical tracking system while referring to the three-dimensional information within the cranium obtained based on the MRI image, a practitioner (such as a doctor) of the transcranial magnetic stimulation treatment is able to guide the treatment coil to the optimum stimulating portion on the patient's head and to apply magnetic stimulation accurately.

Conventionally, when using the optical tracking system in the transcranial magnetic stimulation treatment in such a manner, an infrared reflection marker is provided for each of a static position associated with the patient's head (e.g., a bed in which the patient lies) and the treatment coil, and a current position of the treatment coil is estimated based on a positional relation between these two obtained by detecting the markers, and the treatment coil is guided to the optimum stimulating portion on the patient's head while referring to the three-dimensional information within the cranium obtained based on the MRI image. Therefore, accurate positional alignment between the patient's head and the MRI image is required. Accordingly, accurate positional alignment with the MRI image is performed by specifying the eye, the ear, the nose, or the like using a calibration marker in a state in which the patient's head is fixed to the bed.

Patent Literatures

[Patent Literature 1]: WO 2007/123147
[Patent Literature 2]: JP 2003-180649 A
[Patent Literature 3]: JP 2004-000636 A

SUMMARY OF THE INVENTION

Problems to be Solved by the Invention

However, according to the conventional method, if the patient moves a position and/or a posture of the head after performing the calibration, the accurate positional alignment between the patient's head and the MRI image may be impaired. Therefore, the patient is not allowed to move after the calibration is performed until the magnetic stimulation treatment ends, and this becomes a considerably large strain for the patient. Further, there is a drawback that it is conventionally required to perform the calibration described above prior to the magnetic stimulation treatment, and this is bothersome for the practitioner.

The present invention is made in view of the above problems, and a basic object of the present invention is to provide an image data processing method that is beneficial in order to reduce the patient's strain and botheration for the practitioner when performing the transcranial magnetic stimulation treatment, and a transcranial magnetic stimulation apparatus utilizing the image data processing method.

Means for Solving the Problems

An image data processing device according to a first aspect of the present invention includes: a) a storage means configured to store a three-dimensional MRI image of a subject's head that has been previously taken; b) a three-dimensional appearance image generation means configured to generate a three-dimensional appearance image of the subject's head; c) an image generation means configured to perform positional alignment between the three-dimensional MRI image and the three-dimensional appearance image, and to generate a three-dimensional image of the subject's head after the positional alignment; d) an after-movement image generation means configured to generate, when the subject's head has been moved, a three-dimensional image of the subject's head after the movement and the positional alignment; e) an operational object image generation means configured to generate an image of an operational object indicating a current position of the operational object operated and moved so as to maintain a positional relation with a specific portion on the three-dimensional MRI image of the subject's head; and f) a display means configured to display the three-dimensional image of the subject's head after the movement and the image of the operational object in one image.

An image data processing device according to a second aspect of the present invention is for performing positional alignment between a first image and a second image, the first image being a three-dimensional MRI image of a subject's head, and the second image being a three-dimensional appearance image of the subject's head, the device comprising: a) a selection means configured to select points $m_i$ satisfying a predetermined condition from a plurality of points $b_j$ included in the second image, the points $m_i$ being selected respectively for N points $a_i$ included in the first image; b) a parameter determining means configured to determine, at each of the points $m_i$ selected by the selection means, a rotation matrix R and a parallel translation vector t as parameters for performing rigid-body transformation such that a value of an error function E(R, t) is minimized, the rigid-body transformation converting the points included in the first image into the corresponding points included in the second image, the error function E(R, t) being configured by a predetermined calculation procedure using the rotation matrix R and the parallel translation vector t; and c) a data processing means configured to perform the rigid-body transformation to each of the points $a_i$ using the rotation matrix R and the parallel translation vector t until the value of the error function E(R, t) becomes equal to or smaller than a predetermined threshold value, and to cause the selection means to select the points $m_i$ respectively, for the points $a_i$ after the conversion, and the parameter determining means to determine the rotation matrix R and the parallel translation vector t.

In this case, the selection means may select the points $m_i$ having a smallest Euclidean distance from the plurality of points $b_j$, the points $m_i$ being selected respectively for the N points $a_i$.

In the above case, the error function E(R, t) may satisfy the following expression (Expression 1).

$$E(R, t) = \sum_{i=1}^{N} |Ra_i + t - m_i|$$ [Expression 1]

An image data processing device according to a third aspect of the present invention is for tracking a position and an orientation of a subject's head, and the device includes: a) an image generation means configured to generate a three-dimensional appearance image of the subject's head; b) an extraction and storage means configured to extract at least one characteristic region from the three-dimensional appearance image to store as a three-dimensional template image; c) an after-movement image generation means configured to generate, when the subject's head has been moved, a three-dimensional appearance image of the subject's head after the movement; d) a characteristic region determination means configured to move the template image over the three-dimensional image of the subject's head after the movement, and to determine a position at which correlation between the both image data is maximized as a position of the characteristic region after the movement; and e) a parameter determining means configured to determine a rotation matrix R and a parallel translation vector t as parameters for performing rigid-body transformation such that a value of an error function E(R, t) is minimized, the rigid-body transformation converting points included in the characteristic region before the movement into the corresponding points included in the characteristic region after the movement, the error function E(R, t) being configured by a predetermined calculation procedure using the rotation matrix R and the parallel translation vector t.

In this case, the error function E(R, t) may satisfy the following expression (Expression 2). Here, N is a number equal to or greater than 2 representing a number of feature points included in the characteristic region, $x_i$ represents a three-dimensional position of each of the feature points included in the initial image of the subject's head, $x_i$ represents a three-dimensional position of each of the feature points included in the characteristic region of the three-dimensional image of the subject's head before the movement of the subject's head, $y_i$ represents a three-dimensional position of each of the feature points included in the image of the subject's head after the movement, and $w_i$ represents a weighting coefficient of each of the feature points.

$$E = \sum_{i=0}^{N-1} w_i (Rx_i + t - y_i)^T (Rx_i + t - y_i)$$ [Expression 2]

In the above case, the three-dimensional appearance image of the subject's head may be generated using parallax between images taken from a plurality of viewpoints, or may be generated using a time by which one of light and an ultrasonic wave arrives from one viewpoint.

A transcranial magnetic stimulation apparatus according to a fourth aspect of the present invention is for applying magnetic stimulation to a specific portion within a subject's head using a magnetic-field generation means disposed outside the head, and the apparatus includes: a) the magnetic-field generation means configured to be able to change a position and a posture thereof according to an operation; b) a storage means configured to store a three-dimensional MRI image of a subject's head that has been previously taken; c) a three-dimensional appearance image generation means configured to generate a three-dimensional appearance image of the subject's head; d) an image generation means configured to perform positional alignment between the three-dimensional MRI image and the three-dimensional appearance image, and to generate a three-dimensional image of the subject's head after the positional alignment; e) an after-movement image generation means configured to generate, when the subject's head has been moved, a three-dimensional image of the subject's head after the movement and the positional alignment; f) a magnetic-field generation means image generation means configured to generate an image of the magnetic-field generation means that indicates a current position of the magnetic-field generation means operated so as to maintain a positional relation with a specific portion on the three-dimensional MRI image of the subject's head; and g) a display means configured to display the three-dimensional image of the subject's head after the movement and the image of the magnetic-field generation means in one image.

A transcranial magnetic stimulation apparatus according to a fifth aspect of the present invention is for applying magnetic stimulation to a specific portion within a subject's head using a magnetic-field generation means disposed outside the head, and the apparatus includes an image data processing device for performing positional alignment between a first image and a second image, the first image being a three-dimensional MRI image of a subject's head, and the second image being a three-dimensional appearance image of the subject's head, wherein the image data processing device includes: a) a selection means configured to select points $m_i$ satisfying a predetermined condition from a plurality of points $b_j$ included in the second image, the points $m_i$ being selected respectively for N points $a_i$ included in the first image; b) a parameter determining means configured to determine, at each of the points $m_i$ selected by the selection means, a rotation matrix R and a parallel translation vector t as parameters for performing rigid-body transformation such that a value of an error function E(R, t) is minimized, the rigid-body transformation converting the points included in the first image into the corresponding points included in the second image, the error function E(R, t) being configured by a predetermined calculation procedure using the rotation matrix R and the parallel translation vector t; and c) a data processing means configured to perform the rigid-body transformation to each of the points $a_i$ using the rotation matrix R and the parallel translation vector t until the value of the error function E(R, t) becomes equal to or smaller than a predetermined threshold value, and to cause the selection means to select the points $m_i$ respectively, for the points $a_i$ after the conversion, and the parameter determining means to determine the rotation matrix R and the parallel translation vector t.

In this case, the selection means may select the points $m_i$ having a smallest Euclidean distance from the plurality of points $b_j$, the points $m_i$ being selected respectively for the N points $a_i$.

Further, the error function E(R, t) may satisfy the following expression (Expression 3).

$$E(R, t) = \sum_{i=1}^{N} |Ra_i + t - m_i| \qquad [\text{Expression 3}]$$

A transcranial magnetic stimulation apparatus according to a sixth aspect of the present invention is for applying magnetic stimulation to a specific portion within a subject's head using a magnetic-field generation means disposed outside the head, and the apparatus includes: an image data processing device for tracking a position and an orientation of a subject's head, wherein the image data processing device includes: a) an image generation means configured to generate a three-dimensional appearance image of the subject's head; b) an extraction and storage means configured to extract at least one characteristic region from the three-dimensional appearance image to store as a three-dimensional template image; c) an after-movement image generation means configured to generate, when the subject's head has been moved, a three-dimensional appearance image of the subject's head after the movement; d) a characteristic region determination means configured to move the template image over the three-dimensional image of the subject's head after the movement, and to determine a position at which correlation between the both image data is maximized as a position of the characteristic region after the movement; and e) a parameter determining means configured to determine a rotation matrix R and a parallel translation vector t as parameters for performing rigid-body transformation such that a value of an error function E(R, t) is minimized, the rigid-body transformation converting points included in the characteristic region before the movement into the corresponding points included in the characteristic region after the movement, the error function E(R, t) being configured by a predetermined calculation procedure using the rotation matrix R and the parallel translation vector t.

In this case, the error function E(R, t) may satisfy the following expression (Expression 4). Here, N is a number equal to or greater than two representing a number of feature points included in the characteristic region, $x_i$ represents a three-dimensional position of each of the feature points included in the initial head image, $y_i$ represents a three-dimensional position of each of the feature points included in the head image after the movement, and $w_i$ represents a weighting coefficient of each of the feature points.

$$E = \sum_{i=0}^{N-1} w_i (Rx_i + t - y_i)^T (Rx_i + t - y_i) \qquad [\text{Expression 4}]$$

In the above transcranial magnetic stimulation apparatus, the three-dimensional appearance image of the subject's head may be generated using parallax between images taken from a plurality of viewpoints, or may be generated using a time by which one of light and an ultrasonic wave arrives from one viewpoint.

Effects of the Invention

According to the image data processing device of the first aspect of the present invention, by performing positional alignment between the three-dimensional MRI image of the subject's head and the appearance image of the subject's head, and generating the three-dimensional image of the subject's head after the positional alignment, it is possible to reduce botheration when performing calibration in an initial state in which accurate positional alignment with the MRI image is performed while the subject's head is fixed to bed. Further, as it is possible to perform the positional alignment between the three-dimensional MRI image of the subject's head and the appearance image of the subject's head after the movement, and to automatically obtain the three-dimensional MRI image of the subject's head after moving from the initial state, the accurate positional alignment between the subject's head and the MRI image may not be impaired even if the subject changes the position and/or the posture of the head after performing the calibration in the initial state. Thus, it is possible to significantly reduce the subject's strain. In addition, as the three-dimensional image of the subject's head after the movement and the operational object image are displayed in one image, it is possible to further facilitate the moving operation of guiding the operational object to a predetermined positional relation with respect to a specific portion on the three-dimensional image of the subject's head.

Further, according to the image data processing device of the second aspect of the present invention, it is possible to perform positional alignment between the first image and the second image, the first image being the three-dimensional MRI image of the subject's head, and the second image being the three-dimensional appearance image of the subject's head, there are provided the selection means configured to select points $m_i$ satisfying the predetermined condition from the plurality of points $b_j$ included in the second image, the points $m_i$ being selected respectively for N points $a_i$ included in the first image; and the parameter determining means configured to determine, at each of the points $m_i$ selected by the selection means, the rotation matrix R and the parallel translation vector t as parameters for performing rigid-body transformation such that the value of the error function $E(R, t)$ is minimized, the rigid-body transformation converting the points included in the first image into the corresponding points included in the second image, the error function $E(R, t)$ being configured by the predetermined calculation procedure using the rotation matrix R and the parallel translation vector t.

Moreover, according to the image data processing device of the third aspect of the present invention, there are provided the characteristic region determination means configured to generate, when the subject's head has been moved, the three-dimensional appearance image of the subject's head after the movement, to move the template image over the three-dimensional image of the subject's head after the movement, and to determine the position at which correlation between the both image data is maximized as the position of the characteristic region after the movement; and the parameter determining means configured to determine the rotation matrix R and the parallel translation vector t as parameters for performing rigid-body transformation such that the value of the error function $E(R, t)$ is minimized, the rigid-body transformation converting points included in the characteristic region before the movement into the corresponding points included in the characteristic region after the movement, the error function $E(R, t)$ being configured by the predetermined calculation procedure using the rotation matrix R and the parallel translation vector t. Therefore, it is possible to perform tracking with high speed and high accuracy when tracking the position and the orientation of the subject's head.

Furthermore, according to the transcranial magnetic stimulation apparatus of the fourth aspect of the present invention, by performing positional alignment between the three-dimensional MRI image of the subject's head and the appearance image of the subject's head, and recording the three-dimensional subject's head image after the positional alignment, it is possible to reduce botheration when performing calibration in an initial state in which accurate positional alignment with the MRI image is performed while the subject's head is fixed to bed. Further, as it is possible to perform the positional alignment between the three-dimensional MRI image of the subject's head and the appearance image of the subject's head after the movement, and to automatically obtain the three-dimensional MRI image of the subject's head after moving from the initial state, the accurate positional alignment between the subject's head and the MRI image may not be impaired even if the subject changes the position and/or the posture of the head after performing the calibration in the initial state. Thus, it is possible to significantly reduce the subject's strain. In addition, as the three-dimensional subject's head image after the movement and the operational object image are displayed in one image, it is possible to further facilitate the moving operation of guiding the operational object to a predetermined positional relation with respect to a specific portion on the three-dimensional subject's head image.

Further, the transcranial magnetic stimulation apparatus of the fifth aspect of the present invention is provided with the image data processing device for performing positional alignment between the first image and the second image, the first image being the three-dimensional MRI image of the subject's head, the second image being the three-dimensional appearance image of the subject's head. The image data processing device includes: the selection means configured to select points $m_i$ satisfying the predetermined condition from the plurality of points $b_j$ included in the second image, the points $m_i$ being selected respectively for N points $a_i$ included in the first image; and the parameter determining means configured to determine, at each of the points $m_i$ selected by the selection means, the rotation matrix R and the parallel translation vector t as parameters for performing rigid-body transformation such that the value of the error function $E(R, t)$ is minimized, the rigid-body transformation converting the points included in the first image into the corresponding points included in the second image, the error function $E(R, t)$ being configured by the predetermined calculation procedure using the rotation matrix R and the parallel translation vector t. Therefore, it is possible to perform positional alignment with high speed and high accuracy when performing positional alignment between the first image and the second image.

Moreover, the transcranial magnetic stimulation apparatus of the sixth aspect of the present invention is provided with the image data processing device for tracking the position and the orientation of the subject's head. The image data processing device includes: the after-movement image generation means configured to generate, when the subject's head has been moved, the three-dimensional appearance image of the subject's head after the movement; the characteristic region determination means configured to move the template image over the three-dimensional image of the subject's head after the movement, and to determine the position at which correlation between the both image data is maximized as the position of the characteristic region after the movement; and the parameter determining means configured to determine the rotation matrix R and the parallel translation vector t as parameters for performing rigid-body transformation such that the value of the error function $E(R, t)$ is minimized, the rigid-body transformation converting points included in the characteristic region before the movement into the corresponding points included in the characteristic region after the movement, the error function $E(R, t)$ being configured by the predetermined calculation procedure using the rotation matrix R and the parallel translation vector t. Therefore, it is possible to perform tracking with high speed and high accuracy when tracking the position and the orientation of the subject's head.

Furthermore, according to the present invention, it is possible for the patient to perform treatment at home by his/her own, as a bothersome and specialized operation requiring a practitioner such as calibration may be omitted and restriction of movement of the patient is reduced.

BRIEF DESCRIPTION OF THE DRAWINGS

FIG. 2A is a part of a flowchart for explaining a flow of a magnetic stimulation treatment performed using the apparatus illustrated in FIG. 1.

FIG. 16 shows diagrams for explaining generation of the texture image in the practical example.

EMBODIMENTS OF THE INVENTION

Hereinafter, embodiments of the present invention will be described, taking a case applied to transcranial magnetic stimulation treatment as an example, with reference to the accompanying drawings. It should be noted that an image data processing device according to the present invention may be effectively applied to a region on a subject (e.g., a patient or an examinee) other than the head when providing a magnetic stimulation treatment for treating various diseases.

[Outline of Configuration of Transcranial Magnetic Stimulation Apparatus]

Figure 1:
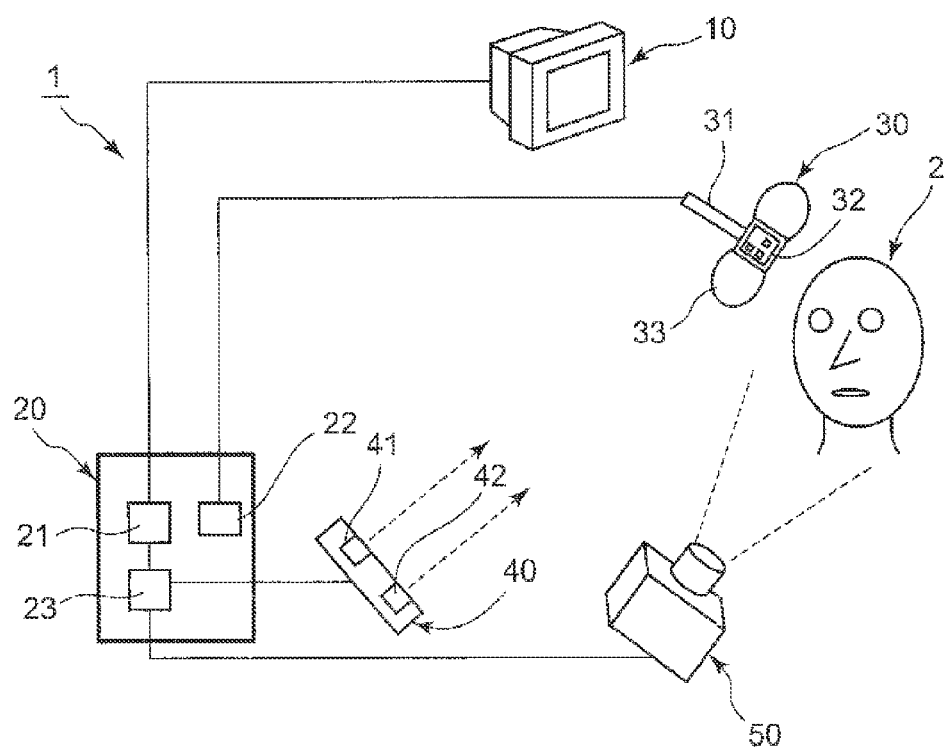
FIG. 1 is a schematic configuration diagram of a transcranial magnetic stimulation apparatus according to one embodiment of the present invention.

FIG. 1 is an explanatory diagram schematically illustrating an outline of a configuration of a transcranial magnetic stimulation apparatus according to the embodiments. A transcranial magnetic stimulation apparatus 1 is for providing a treatment to a specific portion (optimum stimulating portion) of a head 2h of a subject 2 (e.g., the patient or the examinee) by applying magnetic stimulation.

As illustrated in FIG. 1, the transcranial magnetic stimulation apparatus 1 (hereinafter referred to simply as an "apparatus", appropriately) is provided with, as its main component, an image monitor unit 10, an apparatus main body unit 20, a magnetic stimulation coil unit 30, a stereo camera 40, and a projector 50. It should be noted that the stereo camera 40 included in the apparatus 1 is one example for obtaining space coordinate information of a physical object within a three-dimensional space, and can be configured so as to obtain space coordinate information of the face of the subject 2 or the magnetic stimulation coil unit 30 based on a different mode as will be described later.

The image monitor unit 10 includes a monitor screen such as a CRT screen or an LCD screen, and has a function of displaying image information. It is of course possible to use an image display unit of a personal computer. A practitioner of the magnetic stimulation treatment (not depicted) provides a suitable magnetic stimulation treatment by seeing a three-dimensional MRI image of the subject 2 and a position and a posture of the magnetic stimulation coil unit 30 within the space that are displayed in the image monitor unit 10, and by changing the position and the posture of the magnetic stimulation coil unit 30 such that a magnetic flux for magnetic stimulation correctly reaches an optimum stimulating portion. The image monitor unit 10 may display a figure (e.g., see an elongated rectangular shape in FIG. 14 that will be described later) corresponding to the magnetic flux irradiated from the magnetic stimulation coil unit 30 in its screen.

The apparatus main body unit 20 includes components described below integrally on the whole or partially in separate units. It should be noted that these components are provided as a plurality of components for convenience in explanation, and may be realized as execution software installed in a personal computer in actual implementation.

An image display control unit 21 included in the apparatus main body unit 20 readably stores the three-dimensional MRI image of the head 2h of the subject 2 that has been previously taken, and controls display of various images to be displayed in the image monitor unit 10. It should be noted that the three-dimensional MRI image may be readably stored in a memory device provided for the image display control unit 21 or externally for the apparatus main body unit 20. A magnetic stimulation coil control unit 22 controls on/off of the magnetic flux generating current applied to the magnetic stimulation coil unit 30 and controls the current. Further, a three-dimensional information generating unit 23 generates information of a position and a posture of the subject's head 2h and the position and the posture of the magnetic stimulation coil unit 30 within the space using parallax between a plurality of (e.g., two, in this embodiment) images inputted from the stereo camera 40, and controls a random dot pattern projecting operation performed by the projector 50. Each of the image display control unit 21, the magnetic stimulation coil control unit 22, and the three-dimensional information generating unit 23 is configured by a control circuit, a computing circuit, and the like required for the corresponding unit. Specific operations of the image display control unit 21, the magnetic stimulation coil control unit 22, and the three-dimensional information generating unit 23 will be described later.

As described above, the control by this apparatus may be realized as execution software installed in a personal computer, and in this case, this apparatus causes a programmed computer or a computer executing a program recorded in a recording medium to perform required control and computing for control that will be later described. Further, by storing at least a part of programs for executing the required control and the computing described later using the computer, as well as various data necessary for such control and computing in an external server, for example, connected to this apparatus in a manner communication is allowed, and downloading the programs and the various data as required in response to a request from a side of the apparatus, the required control or the computing may be executed using the computer.

The magnetic stimulation coil unit 30 is for providing a magnetic stimulation treatment of giving magnetic stimulation to an optimum stimulating portion by applying a magnetic flux of a predetermined intensity to generate an induced current within the brain of the subject's head 2h by the practitioner operating an operating unit that is not depicted to operate the magnetic stimulation coil control unit 22 while the practitioner holding a holding portion 31 and changing the position and the direction (posture) freely within a predetermined range of space to move it closer to the optimum stimulating portion in an appropriate manner. For this reason, the magnetic stimulation coil unit 30 is provided with a magnetic stimulation coil 33 (hereinafter referred to as a "treatment coil", or simply as a "coil" as needed), and a marker unit 32 with which the stereo camera 40 generates a parallax image and information of the position and the posture of the magnetic stimulation coil unit 30 (that is, a position and a posture of the treatment coil 33). As will be described later, the marker unit 32 has a specific figure pattern.

As used herein, "the posture of the treatment coil" refers to a direction and an angle of the treatment coil 33, "the direction of the treatment coil" refers to an orientation of the coil 33 on the surface of a scalp of the subject's head 2h, and "the angle of the treatment coil" refers to an angle between a normal line of the surface of the scalp of the subject's head 2h and a magnetic field direction of the coil 33.

The stereo camera 40 takes images of the photogenic subjects using the imaging cameras 41 and 42 on left and right and outputs images of the respective photogenic subjects, in order to detect the positions and the orientations of the subject's head 2h and the magnetic stimulation coil unit 30 within the space based on parallax between two images outputted from the imaging cameras 41 and 42 provided in pair on left and right.

Further, the projector 50 projects a random dot pattern over the surface of the subject's head 2h to provide an extraction point for image processing.

[Characteristics of this Transcranial Magnetic Stimulation Apparatus]

In order to overcome the technical problems involved with the conventional transcranial magnetic stimulation apparatus, the inventors of this application analyzed requirements expected for the transcranial magnetic stimulation apparatus 1, and obtained the following knowledge.

First, in order to provide the magnetic stimulation treatment, it is required to perform accurate positional alignment between a three-dimensional taken image and three-dimensional MRI data of the subject's head 2h. In order to perform such accurate positional alignment without restricting movement of the subject 2, a process of analyzing the position and the orientation (posture) of the subject's head 2h that continuously change over time so that the MRI data always matches the image of the head is necessary. In this embodiment, a three-dimensional face image of the face of the subject 2 including a large number of feature points that can be easily specified is used as a three-dimensional appearance image of the head 2h of the subject 2.

Further, it is also necessary to analyze the position and the posture of the magnetic stimulation coil unit 30 for providing the magnetic stimulation, and always grasp which region of the brain of the subject's head 2h is to be stimulated.

Moreover, as the practitioner (such as a doctor) is required to provide stimulation while referring to the information within the cranium based on the three-dimensional MRI image (an image of the surface of the brain), an interface for displaying the information of the brain surface, the posture of the head (face), and the posture of the magnetic stimulation coil unit 30 in an easily understandable manner is also necessary.

Putting the above all together, the requirements to be filled when constructing the transcranial magnetic stimulation apparatus 1 are as follows.

(1) A function for verifying postures of three-dimensional MRI measurement data and a current posture of the head (face) of the subject 2 should be provided.

(2) A function for tracking the posture of the head (face) of the subject 2 in real time should be provided.

(3) A function for tracking the position and the posture of the magnetic stimulation coil unit 30 in real time should be provided.

(4) An interface function with which a situation of the stimulation is easily grasped such as magnetic stimulation points on the brain surface should be provided.

It is important to realize these four requirements with sufficient accuracy, operability, and an economic efficiency.

Thus, the transcranial magnetic stimulation apparatus 1 according to this embodiment is configured as an apparatus such that by using optical devices such as a means exemplified by the stereo camera 40 for obtaining information of space coordinates of a physical object within the three-dimensional space and an image projector device (the projector 50) for projecting random dots to the subject's head 2h to provide a marker for positional measurement, thereby, the changes in the head posture and the face shape are measured automatically only by the subject 2 taking a posture at rest during an examination to visualize the situation of the magnetic stimulation of the treatment coil 33.

According to such a constitution, it is possible to grasp the position within the three-dimensional space based on the parallax using the stereo camera 40, or the position within the three-dimensional space using a different means, thereby, a limit for grasping the positions of the subject's head 2h and the treatment coil 33 is expanded to a range within the three-dimensional space in which the position can be grasped, such as an limiting area of image-picking of the stereo camera 40. In addition, as a limit in which the position at which the subject 2 lies still and the treatment coil 33 can be moved is expanded, a convenience for the treatment (procedure) may be improved and the strain on the subject 2 may be reduced. Further, as it is a position grasping method similarly using the stereo camera 40, the subject 2 may not be restricted its movement or attached with a fixing unit, and thus the strain may be reduced.

[Basic Operation of Transcranial Magnetic Stimulation Apparatus]

A basic operation of the transcranial magnetic stimulation apparatus 1 having the components illustrated in FIG. 1 will be specifically described. It should be noted that in the following description, functions and operations are described focusing a procedure and a method for processing such as specific calculation for the image processing, and therefore functions and operations of the components of the apparatus 1 previously described with reference to FIG. 1 may not be directly referred. However, even in such a case, the described functions and operations are realized as the functions and operations of the transcranial magnetic stimulation apparatus 1 illustrated in FIG. 1, and thus their correspondence with the components of the apparatus 1 may be easily determined.

An operation of guiding the treatment coil 33 to an optimum position (that is, a position corresponding to the optimum stimulating portion in the subject's head 2h) and a posture using the apparatus 1 includes four steps roughly classified as listed blow.

Figure 2B:
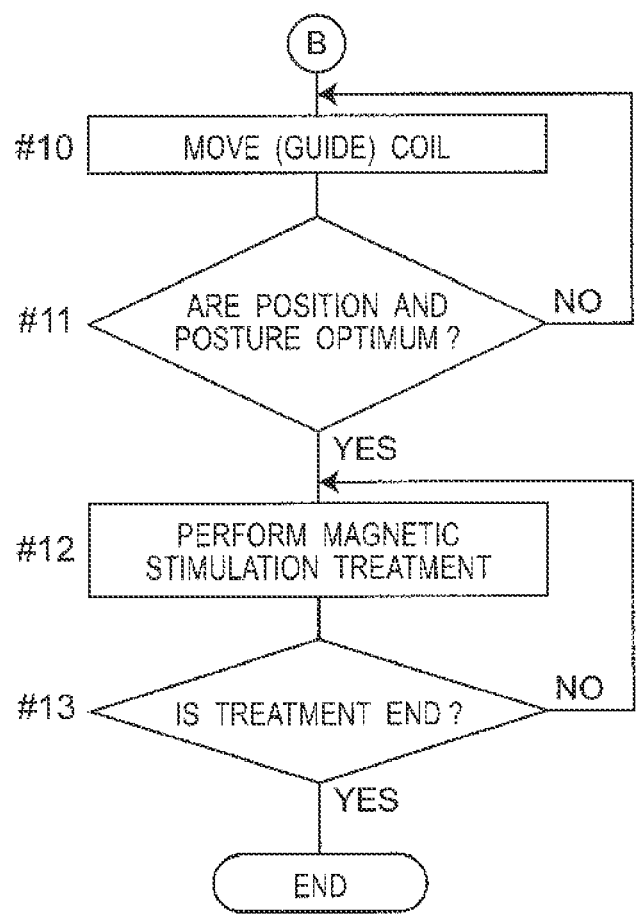
FIG. 2B is a part of the flowchart for explaining the flow of the magnetic stimulation treatment.

(I) Initial positional alignment
(II) Tracking of the posture of the subject's head
(III) Tracking of the treatment coil
(IV) Displaying of the tracking result FIG. 2A and FIG. 2B are flowcharts for explaining a flow of the magnetic stimulation treatment using the apparatus 1, including the operation of guiding the treatment coil 33 to the optimum position.

As the operation of the apparatus 1 starts, first, in step #1, an image frame (initial image frame) including the subject's head 2h and the magnetic stimulation coil unit 30 is obtained using, for example, the stereo camera 40, and then, in step #2, initial positional alignment between a three-dimensional face image of the subject 2 in an initial state obtained based on the initial image frame and a three-dimensional MRI image of the subject's head 2h readably stored in the image display control unit 21 of the apparatus main body unit 20 is performed. These steps correspond to "(I) Initial positional alignment" step described above.

More specifically, using an ICP algorithm (a method for obtaining a rigid-body transformation parameter that minimizes a distance between correspondence points by iterative calculation), matching on the same coordinate system between MRI data of the head of a patient receiving the treatment and face shape data of the patient based on, for example, the stereo measurement is performed. Details of the initial positional alignment step will be described later. It should be noted that in this embodiment, as described above, the three-dimensional face image of the face of the subject 2 including a large number of feature points that can be easily specified is used as the three-dimensional appearance image of the head 2h of the subject 2.

After the initial positional alignment described above is completed, image frames are continuously obtained using the stereo camera 40 (step #3) from moment to moment, for example, and a current three-dimensional face image of the subject 2 is obtained based on a current image frame that has been obtained (step #4). In other words, real time tracking of the posture of the subject's head 2h is performed. Then, verification of three-dimensional position and posture of the three-dimensional MRI image of the subject's head 2h is performed for the current three-dimensional face image of the subject 2 (step #5). With this, a current three-dimensional MRI image of the subject's head 2h is obtained.

At this time, reflecting a result of the initial positional alignment in step #2 on a result of the real time tracking of the posture of the subject's head 2h, it is possible to superimpose the current three-dimensional face image and the three-dimensional MRI image of the subject 2 at a correct position and a correct posture. The steps from step #4 and step #5 correspond to "(II) Tracking of the posture of the subject's head" step described above.

On the other hand, for the treatment coil 33, based on the current image frame obtained in step #3, current marker information of the treatment coil 33 (that is, image information of the marker unit 32 for tracking attached to the magnetic stimulation coil unit 30) is obtained (step #6). By tracking the marker unit 32, tracking of the position and the posture of the coil 33 is performed. Then, current three-dimensional position and posture of the marker unit 32 are calculated based on the marker information (step #7), and current three-dimensional position and posture of the coil 33 (preferably, three-dimensional position and direction of a magnetic field) are calculated (step #8). The steps from step #6 through step #8 correspond to "(III) Tracking of the treatment coil" step described above.

Then, based on a result of step #5 and a result of step #8, at least the current three-dimensional MRI image of the subject's head 2h and the current three-dimensional position and posture of the coil 33, and more preferably, the current face image and the current three-dimensional position and direction of the magnetic field in addition, are displayed in a three-dimensional image representing the same space (step #9). The step of step #9 corresponds to "(IV) Displaying of the tracking result" step described above. It should be noted that, as described above, the three-dimensional position and the direction of the magnetic field may be displayed on the screen using the figure corresponding to the magnetic flux irradiated from the treatment coil 33 (e.g., see the elongated rectangular shape in FIG. 14 that will be described later).

In this manner, by reflecting the tracking result of the treatment coil 33 and the tracking result of the posture of the subject's head 2h in the display, it is possible to display the current position and posture of the treatment coil 33, that is, the region of the brain surface of the subject 2 to which the magnetic flux for treatment is directed.

A series of the steps from step #3 through step #9 is executed constantly and repeatedly until the magnetic stimulation treatment is completed and the apparatus 1 stops.

Next, in step #10, the coil 33 is guided by being moved to an optimal stimulation position and posture while referring to the three-dimensional image obtained in step #9, and it is determined whether or not the current three-dimensional position and posture of the coil 33 (preferably, the three-dimensional position and direction of the magnetic field) has reached the optimum position (position corresponding to the optimum stimulating portion of the subject's head 2h) and posture (step #11). Then, upon arrival at the optimum position and posture (step #11: YES), the magnetic stimulation treatment using the coil 33 is performed (step #12). Specifically, the practitioner activates the magnetic stimulation coil control unit 22 to apply a magnetic flux of a predetermined intensity from the treatment coil 33 and generate an induced current within the brain of the subject's head 2h, and applies magnetic stimulation to the optimum stimulating portion.

Then, the magnetic stimulation treatment is continuously performed until the magnetic stimulation treatment is completed when a predetermined treatment effect is provided (or when a predetermined time has passed) (step #13: NO), and the apparatus 1 stops its operation upon completion of the magnetic stimulation treatment (step #13: YES). In this manner, a series of the steps from step #3 through step #13 is executed continuously and repeatedly until the treatment is completed and the apparatus 1 stops its operation.

Next, the steps of "initial positional alignment", "tracking of the posture of the subject's head", "tracking of the treatment coil", and "display of the tracking result" described above will be described in more detail.

[(I) Step of Initial Positional Alignment]

Figure 3:
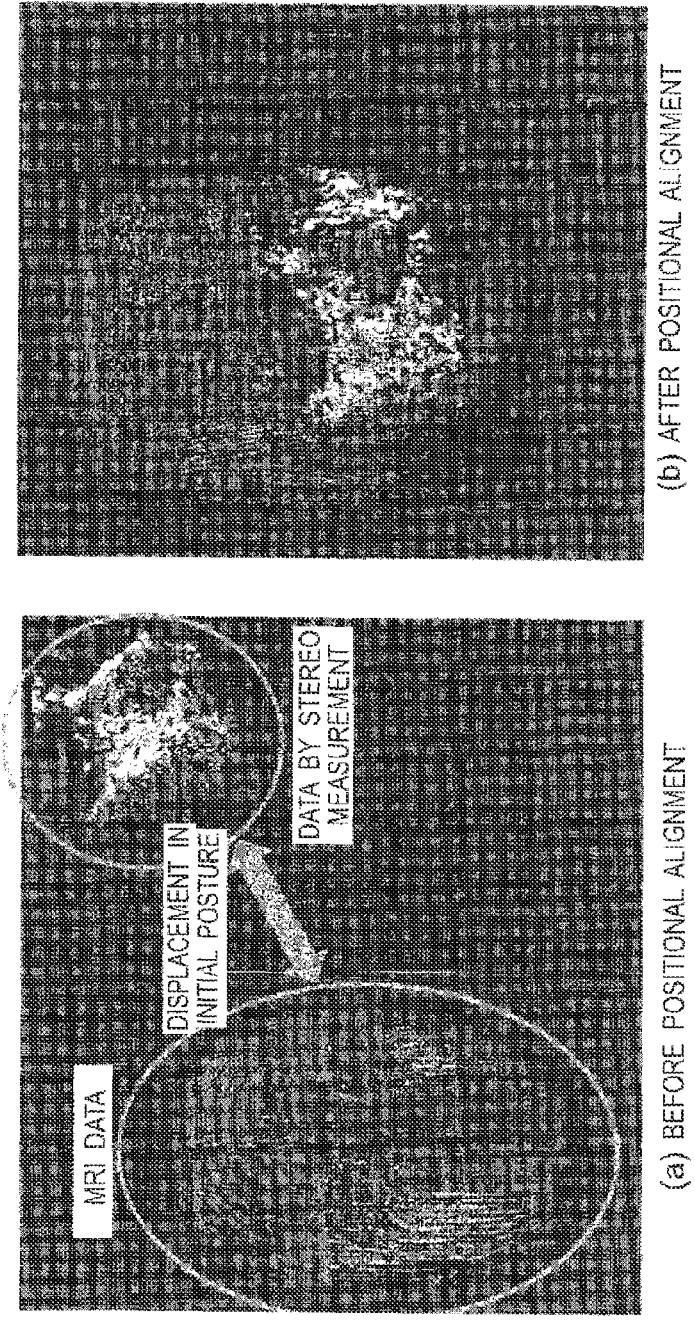
FIG. 3 shows views for explaining a process of performing positioning of a three-dimensional MRI image of the head and a three-dimensional appearance image of the head using the apparatus illustrated in FIG. 1.

The head MRI image data obtained by an MRI apparatus installed in a medical facility prior to the magnetic stimulation treatment, and the measurement data obtained based on the stereo measurement using the stereo camera 40 as one example of the apparatus 1 (three-dimensional position measurement using parallax) are measured using different measurement apparatuses with different postures of a patient, and displacement occurs between the data of the two types when three-dimensionally displayed in the same coordinate system (see FIG. 3(a)). Accordingly, it is necessary to match the data of the two types. The data of the two types after positional alignment is illustrated in FIG. 3(b).

This process is called positional alignment, and corresponding to obtaining a 3 by 3 rotation matrix R and a three-dimensional parallel translation vector t, as rigid-body transformation parameters for determining the posture for each data. For the apparatus 1, the ICP (Iterative Closest Point) algorithm is used as the positional alignment method. This algorithm is a method for obtaining a rigid-body transformation parameter that minimizes a distance between correspondence points by iterative calculation. By using this method, it is possible to perform the positional alignment, with high accuracy, without requiring correspondence between the measurement data or prior calibration of the measurement apparatus and the physical object.

The initial positional alignment is performed by executing the process in the following order.

(1) The MRI data is read.

(2) The face is captured using two cameras (the left camera 41 and the right camera 42)

(3) The face detection using Adaboost (described later) is performed to the images obtained by the left and right cameras 41 and 42 to extract face regions from the images.

(4) The stereo measurement is performed to the face regions to measure a face shape.

(5) The positional alignment between the MRI data and face shape data obtained through the stereo measurement is performed using the ICP algorithm.

<Stereo Measurement>

Hereinafter, the stereo measurement used by the apparatus 1 which is one embodiment of the three-dimensional position detection method will be described.

The stereo measurement is one type of an optical three-dimensional shape measurement method, in which images of a measurement object are taken by two cameras on left and right, and a three-dimensional position is estimated from parallax information based on a triangulation method. The stereo measurement requires two processes of (a) searching of correspondence points and (b) calculation of the three-dimensional position.

(a) Searching of Correspondence Point

When a three-dimensional position is obtained using the triangulation method, it is necessary to obtain displacement between the correspondence points (parallax) after finding out which point in an image taken by the left camera 41 corresponds to which point in an image taken by the right camera 42.

Figure 4:
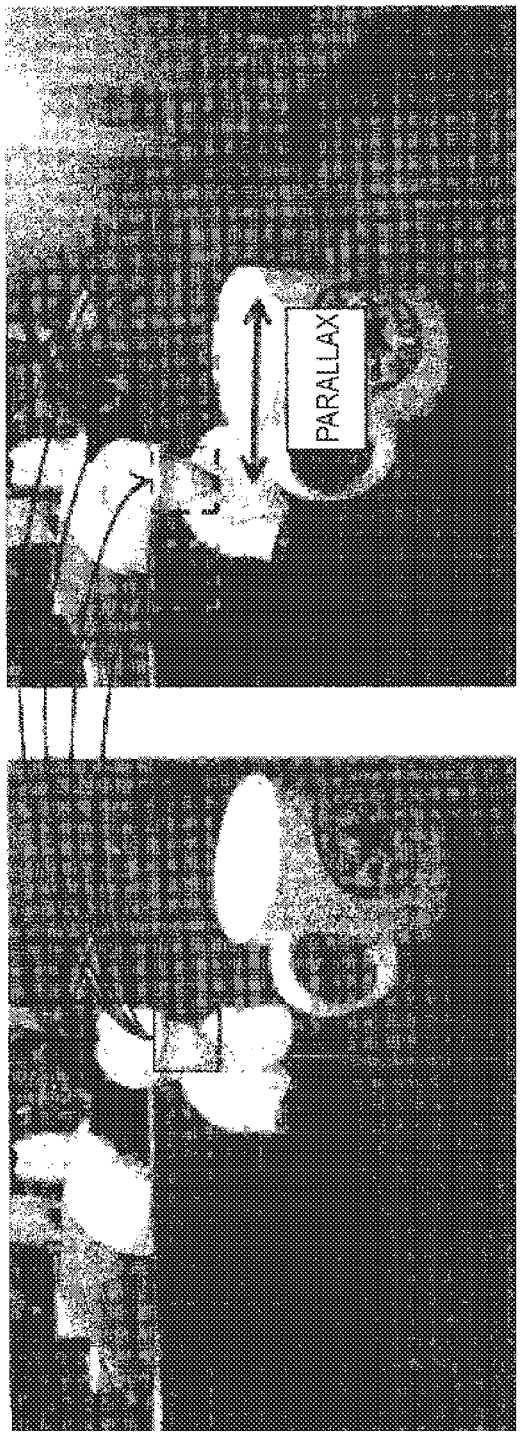
FIG. 4 shows views for explaining an operation of three-dimensional position sensing based on parallax using the apparatus illustrated in FIG. 1.

FIG. 4 shows an example of the two images on left and right used in the stereo measurement. The stereo camera 40 used in this embodiment is based on parallel stereogram (an optical axis of the right camera 42 and an optical axis of the left camera 41 are parallel), and therefore displacement between the correspondence points occurs only in a lateral direction. Therefore, in the correspondence point searching, only the lateral direction has to be considered, and all of the correspondence points in a right eye image when viewed in a left eye image are on a side leftward as compared to those in a left eye image.

Block matching is used for correspondence point searching. The block matching is a method in which each of inputted images is taken as a two-dimensional array having pixel values, a small region centering a pixel in focus in the left image is superimposed over the right image while moving along the right image, a difference between the pixel values is obtained, and one of such regions whose sum of squares of the difference (SSD) is smallest is taken as a correspondence point.

A specific calculation method for this block matching will be now described. In the image taken by the left camera, a pixel value that is x-th in the lateral direction and y-th in a longitudinal direction is taken as $I_{left}(x, y)$. In the image taken by the right camera, a pixel value that is x-th in the lateral direction and y-th in the longitudinal direction is taken as $I_{right}(x, y)$. In addition, a size of a block to be compared is taken as m×m. Further, the displacement in a searching direction is taken as d, and the calculation in the block matching is performed by comparing $I_{left}(x, y)$ with $I_{right}(x, y)$. In other words, the SSD is calculated by the following expression (Expression 5), and the displacement d when the SSD is smallest is obtained. A value of d at this time is a parallax value desired to be obtained.

$$SSD = \sum_{i=-\frac{m}{2}}^{\frac{m}{2}} \sum_{j=-\frac{m}{2}}^{\frac{m}{2}} (I_{left}(x+i, y+j) - I_{right}(x+i-d, y+j))^2 \quad [\text{Expression 5}]$$

(b) Calculation of Three-Dimensional Position

Using the parallax d obtained through the correspondence point searching described above, the three-dimensional position is calculated based on the known triangulation method.

Figure 5:
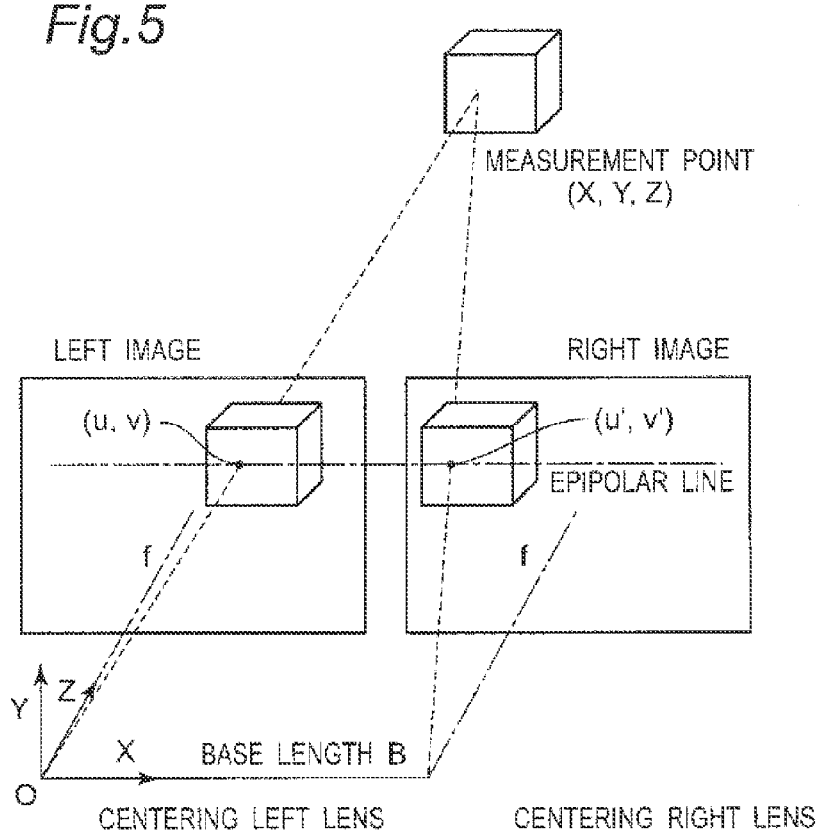
FIG. 5 is an explanatory diagram illustrating a relation between three-dimensional positions of parallel stereogram and a measurement object when performing the three-dimensional position sensing based on the parallax.

FIG. 5 illustrates by example a relation between the three-dimensional positions of the parallel stereogram and the measurement object. In the parallel stereogram, as the correspondence point is located on the horizon, a depth may be calculated as a reverse proportion of the parallax. A three-dimensional position of a point of regard may be calculated by the following expression (Expression 6).

Here, B represents a distance between the cameras, and f represents a focal length of each camera. As values of B and f are known in the measurement, it is possible to calculate the three-dimensional position of the point of regard using the parallax d determined through the correspondence point searching.

$$\begin{bmatrix} X \\ Y \\ Z \end{bmatrix} = \begin{bmatrix} uB/d \\ vB/d \\ fB/d \end{bmatrix} \quad [\text{Expression 6}]$$

<Face Detection Based on Adaboost Method>

In the positional alignment between the MRI data and the data obtained by the stereo measurement, only the three-dimensional data of the face surface is used. For the MRI data, only the necessary region is extracted in advance. On the other hand, for the stereo measurement data, the face regions are detected in the images obtained by the camera 40, and the three-dimensional data for these regions are used. With the apparatus 1, object detection using a Haar-like feature amount as an image feature amount and an Adaboost algorithm as a learning algorithm is used as a face extraction process. This object detection process is an improvement by Rainer Lienhart and others (Rainer Lienhart and Jochen Maydt: "An Extended Set of Haar-like Feature for Rapid Object Detection", IEEE ICIP 2002, vol. 1, pp. 900-903 (2002)) based on the research of the object detection by Paul Viola and others (Paul Viola and Michael Jones: "Object Detection using a Boosted Cascade of Simple", IEEE CVPR, 2001), and allows high speed detection of an object.

<ICP (Iterative Closest Point) Algorithm>

The ICP algorithm is used as the method for positional alignment between the MRI data and the data obtained in the stereo measurement. The ICP algorithm is a method proposed by Besl and others in 1992 (P. J. Besl and N. D. McKay: "A Method for Registration of 3-121 Shapes", IEEE Trans. Pattern Anal. Machine Intell, vol. 14, No. 2, pp. 239-256 (1992-2)), and for obtaining a rigid-body transformation parameter that minimizes a distance between the correspondence points by iterative calculation.

A Euclidean distance d between two points $r_1$ and $r_2$ within three-dimensional space may be represented as in the following expression (Expression 7).

$$\vec{r_1} = (x_1, y_1, z_1), \vec{r_2} = (x_2, y_2, z_2)$$
$$d(r_1, r_2) = \sqrt{(x_1 - x_2)^2 + (y_1 - y_2)^2 + (z_1 - z_2)^2}$$
[Expression 7]

Figure 6:
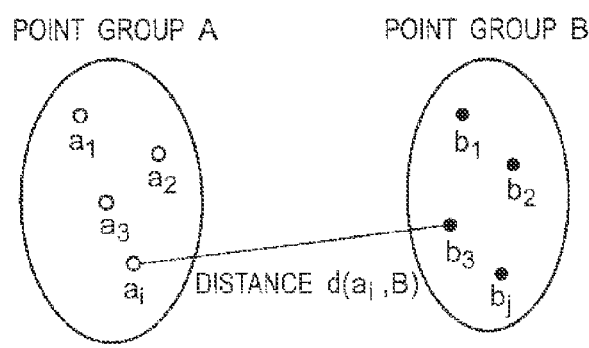
FIG. 6 is a schematic diagram for explaining a positional alignment method of figures within a three-dimensional space used by the apparatus illustrated in FIG. 1.

Here, it is assumed that there are two point sets of a point set A including N points $a_i$ and a point set B including M points $b_j$ (see the following expression (Expression 8) and FIG. 6).

$$A = \vec{a_i}, i=1,2,\ldots N$$
$$B = \vec{b_j}, j=1,2,\ldots M$$
[Expression 8]

Figure 7:
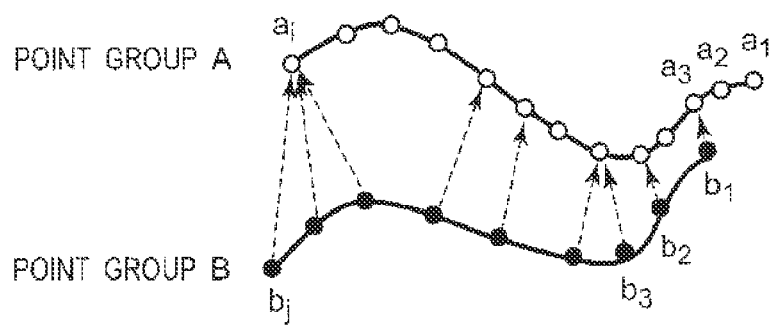
FIG. 7 is a schematic diagram for explaining the positional alignment method of figures within the three-dimensional space.

Distances between the points $a_i$ included in the point set A and the point set B are defined as a distance between the points $a_i$ and one of the points included in the point set B that is closest in distance (see the following expression (Expression 9) and FIG. 7), and a distance $d(a_i, B)$ between each of the points $a_i$ included in the point set A and the point set B is obtained.

$$d(a_i, B) = \min_{j=1\ldots M} d(a_i, b_j)$$
$$= d(a_i, m_i)$$
[Expression 9]

Where points corresponding to the points $a_i$ are represented by $m_i \in B$, the rotation matrix R and the parallel translation vector t as the rigid-body transformation parameters may be obtained by minimizing an error function $E(R, t)$ represented by the following expression (Expression 10).

It should be noted that the expression (Expression 10) is the same as the expressions (Expression 1) and (Expression 3) described previously.

$$E(R, t) = \sum_{i=1}^{N} |Ra_i + t - m_i|$$
[Expression 10]

Putting the above processes all together, it is possible to obtain the rigid-body parameters for the positional alignment through the following procedures.

(i) A closest point $m_i$ is obtained for each of the points $a_i$ in the point set A to the point set B.

(ii) The rigid-body transformation parameters that minimizes an error E are obtained.

(iii) The point set A is converted using the parameters (R, t).

(iv) The iterative calculation is terminated if the error E is smaller than a threshold value. Otherwise, the process returns to (i), and the same steps are repeatedly executed.

In implementation of the present invention, the method of determining the rigid-body transformation parameters is a mere example, and a different method may be used for the point in which a point whose distance is the smallest is taken as a start for approximate calculation and for the error calculation method indicated by Expression 5. Any method may be used as long as numerical evaluation of a degree of matching of a position and a posture of a rigid body (six-degree-of-freedom) within the three-dimensional space, that is, a magnitude of the error, is performed. This also applies in the description hereinafter.

Other Examples for Obtaining Position Information within Three-Dimensional Space While as the method for obtaining the position information of the face of the subject 2 and the magnetic stimulation coil unit 30 within the three-dimensional space, the parallax of the stereo camera 40, that is, the parallax of the images taken from a plurality of viewpoints is used in the above description (first example), the present invention is not limited to such a method, and it is possible to obtain the position information using other examples.

As a second example, it is possible to use a light projecting means such as a projector or a laser irradiation means, an imaging means such as a video camera having only a single viewpoint (not a method utilizing parallax between the images taken from a plurality of viewpoints). In a state in which light emitted from the light projecting means is reflected upon a physical object, and the reflected light is captured by the imaging means, it is possible to determine a distance to and an angle with the physical object from the angle information of each of the optical axes based on the same triangulation principle described above. Consequently, it is possible to obtain the space coordinates of a light reflection point of the physical object.

Further, as a third example, it is possible to obtain the space coordinate information of each point of the physical object from information of the distance and information of the projecting angle of the projection light or the ultrasonic waves by combining a distance meter utilizing laser light or ultrasonic waves for determining a distance of the physical object point and a scanning means for scanning the measured point. As the above distance meter, a laser radar (that determines the distance of the physical object by measuring a time period during which the laser projection light reflects on the physical object and returns to a light receiving sensor) or an ultrasonic wave distance meter (that similarly utilizes a time period for ultrasonic waves that has been projected returns) may be used.

Moreover, as a fourth example, an apparatus for taking an image of a photogenic subject as a measurement physical object by an imaging means and calculating a distance of a photogenic subject point in an image produced in each pixel within a screen of the taken image is commercially available. With the apparatus, an image of a photogenic subject as a measurement physical object is taken by an imaging means using a solid-state image pick-up device such as a CCD. And the apparatus senses a time period during which light similarly projected from the light projecting means to the photogenic subject is reflected and reaches each picture element (pixel) in the solid-state image pick-up device based on a light phase difference between the projection light and the light that has reached the pixels, and consequently calculates a distance of a photogenic subject point in an image produced in each pixel within a screen of the taken image. For example, MESA Imaging AG in Zurich, Switzerland has introduced an apparatus by the product name of "SR4000" into the market, and the technique related to this product is disclosed, for example, in JP 2009-515147 A.

Not limited to the method using the parallax of the stereo camera, the methods according to the "other examples (second to fourth examples)" as described above may be utilized in order to obtain the position information within the three-dimensional space, and this similarly applies in the description hereinafter.

[(II) Tracking Step of Posture of Subject's Head]

As described above, the MRI data and the data obtained from the stereo measurement are brought into a state in which their initial states in the same coordinate system match by using the ICP algorithm. Here, in order to perform the magnetic stimulation without restricting the movement of the subject 2, it is necessary to track a change of the subject's head 2h from the initial posture in real time, and to obtain the rigid-body transformation parameters to the current posture.

It should be noted that as described above, in this embodiment, a three-dimensional face image of the face of the subject 2 including a large number of feature points that can be easily specified is used as the three-dimensional appearance image of the head 2h of the subject 2. Therefore, in this case, "the posture of the subject's head 2h" may be expressed as "face posture" of the subject 2.

For the initial state, as described above, the ICP algorithm is used for obtaining a rigid-body transformation parameter for the positional alignment. According to this method, it is possible to match the point sets whose correspondence is unknown with high accuracy. However, as considerable iterative calculation is required and it takes time for the process, this method is not suitable for the process of tracking the face posture in real time after the initial positional alignment is completed.

On the other hand, if the correspondence between the point sets is known, by using a method according to this correspondence, for example, a template matching method described below, it is possible to significantly reduce a calculation amount and to reduce time and cost required for the calculation as compared to the case in which the ICP algorithm is used.

Thus, in this embodiment, seven points including the inner and outer corners of both eyes, the corners of mouth (both ends), and the tip of nose are specified as face characteristics, and the rigid-body transformation parameters are calculated by tracking these face characteristics using template matching. A criterion of selection of a face characteristic region is based on a pattern that is characteristic among the face image and suitable for tracking.

Hereinafter, a specific process procedure for the real time tracking step of the face posture will be described.

(1) The face image in the initial posture is obtained using the stereo camera.

(2) Each of the characteristic regions (the inner and outer corners of both eyes, the corners of mouth (both ends), and the tip of nose) is specified, and images of the regions (templates) and the three-dimensional coordinates are stored.

(3) The face images in the current posture are obtained using the stereo camera.

(4) The position of the feature point included in the left image and the right image is found out using template matching, and obtaining its three-dimensional coordinates.

(5) The change from the initial posture is obtained based on a steepest descent method (that is, obtaining the rigid-body transformation for fitting the measured value in the initial posture to the current posture).

Here, the processes (1) and (2) are initialization processes and may be performed just once when starting the tracking. The face tracking performed in real time is performed by repeatedly performing the processes (3) to (5).

<Template Matching>

Now, the template matching method will be described.

Figure 8:
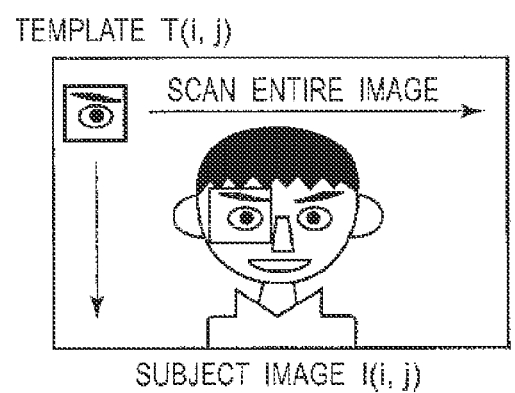
FIG. 8 is a schematic diagram for explaining a template matching method used by the apparatus illustrated in FIG. 1.

The template matching is a process of making correspondence regarding a portion in one image at which a different image (template) presents. As illustrated in FIG. 8, this method is such that an image called a template is previously prepared and superimposed over the subject image while moving the template to find out correlation between the template and the subject image.

As a scale for measuring a difference between the two images, a correlation coefficient C is used. The correlation function C is expressed by the following expression (Expression 11), where the subject image is I(m, n) and the template image is T(m, n) (image size: M×N). At this time, the greater a value of the correlation coefficient C is, the greater the correlation between the images, and a region having a largest correlation coefficient within the image is determined to be a corresponding region.

$$C = \frac{\sum_{j=1}^{M}\sum_{i=1}^{N} \phi(i,j)\varphi(i,j)}{\sqrt{\sum_{j=1}^{M}\sum_{i=1}^{N} \phi(i,j)^2 \sum_{j=1}^{M}\sum_{i=1}^{N} \varphi(i,j)^2}}$$ [Expression 11]

$$\phi(i,j) = I(i,j) - \frac{\sum_{j=1}^{M}\sum_{i=1}^{N} I(i,j))}{NM}$$

$$\varphi(i,j) = T(i,j) - \frac{\sum_{j=1}^{M}\sum_{i=1}^{N} T(i,j))}{NM}$$

<Face Posture Calculation by Optimization Calculation>

Figure 9:
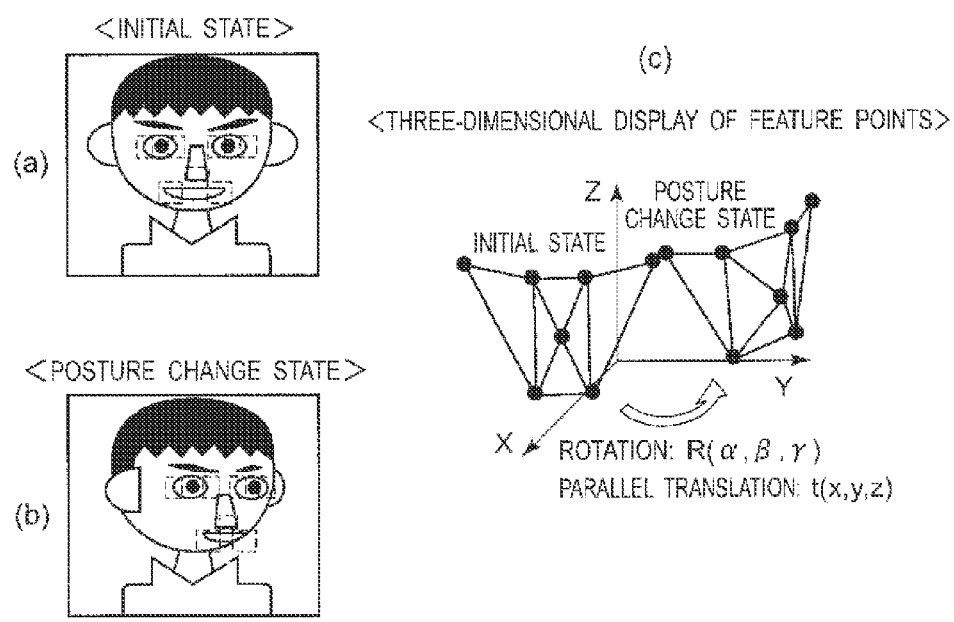
FIG. 9 is a schematic diagram for explaining the template matching method.

In order to perform tracking of the face posture, it is necessary to obtain the change in the posture from the initial posture. According to the apparatus 1, as described above, the posture tracking for obtaining three-dimensional changes in the posture of the seven points of the characteristic regions including the inner and outer corners of both eyes, the corners of the mouth (both ends), the tip of nose (a rotation R(α, β, γ) and a parallel translation t(x, y, z)) is performed (see FIG. 9).

First, the posture in the initial positional alignment described above is taken as the initial posture, and the three-dimensional coordinates of the characteristic region are obtained based on the stereo view. Then, searching of the face characteristic region is performed to a current frame by the template matching, and as a result of the stereo view, the three-dimensional coordinates of each region is obtained.

Next, a problem of obtaining the position and the posture of the head based on a result of the measurement of the three-dimensional position of each characteristic region results in a problem of obtaining the rotation matrix R and the parallel translation vector t as the rigid-body transformation parameters that minimize the error function E shown in the following expression (Expression 10). It should be noted that the expression (Expression 12) is the same as the expressions (Expression 2) and (Expression 4) described previously.

$$E = \sum_{i=0}^{N-1} w_i (Rx_i + t - y_i)^T (Rx_i + t - y_i)$$ [Expression 12]

Here, N represents a number of the feature points, xi represents the three-dimensional position of each feature point in the initial posture, and yi represents the three-dimensional position of each characteristic region in the current face posture. Further, wi represents a weighting coefficient of each feature point, and a product of correlation coefficients obtained when the characteristic regions are detected from the left image and the right image using the template matching is used for this coefficient. In this embodiment, the rigid-body transformation is obtained using a so-called steepest descent method.

[(III) Step of Tracking Treatment Coil]

In order to perform the magnetic stimulation treatment, it is necessary to grasp the three-dimensional position and posture of the treatment coil 33, and to constantly watch if the stimulation is accurately applied to the subject. Typically, the accuracy effective for the magnetic stimulation treatment is a diameter of about 1 cm in within the cranium, and it is necessary to direct a magnetic flux beam from the treatment coil 33 targeting this spot. In the tracking of the treatment coil 33, a known marker (a figure pattern provided on the surface of the photogenic subject in order to extract the feature point from the image data) is used, and the three-dimensional position and posture of the coil 33 is obtained by tracking the marker.

A specific process is described below.

(1) The image is obtained using the stereo camera 44.

(2) The marker recognition is performed to the left image and the right image, and pixels at four corners of a marker 32 are searched.

(3) Three-dimensional positions of the four corners of the marker 32 are obtained by the stereo view.

(4) A normal line vector in a marker plane is obtained, and the direction of the magnetic flux (stimulation direction) is obtained.

<Recognition of Marker>

The most important technique in the tracking of the treatment coil 33 is to accurately grasp a marker region within the image. In the marker recognition, it is necessary to previously register the marker 32 to be used, and a marker candidate region in the searching image is searched, and the marker region is defined by finding out correlation with the registered marker.

Figure 10:
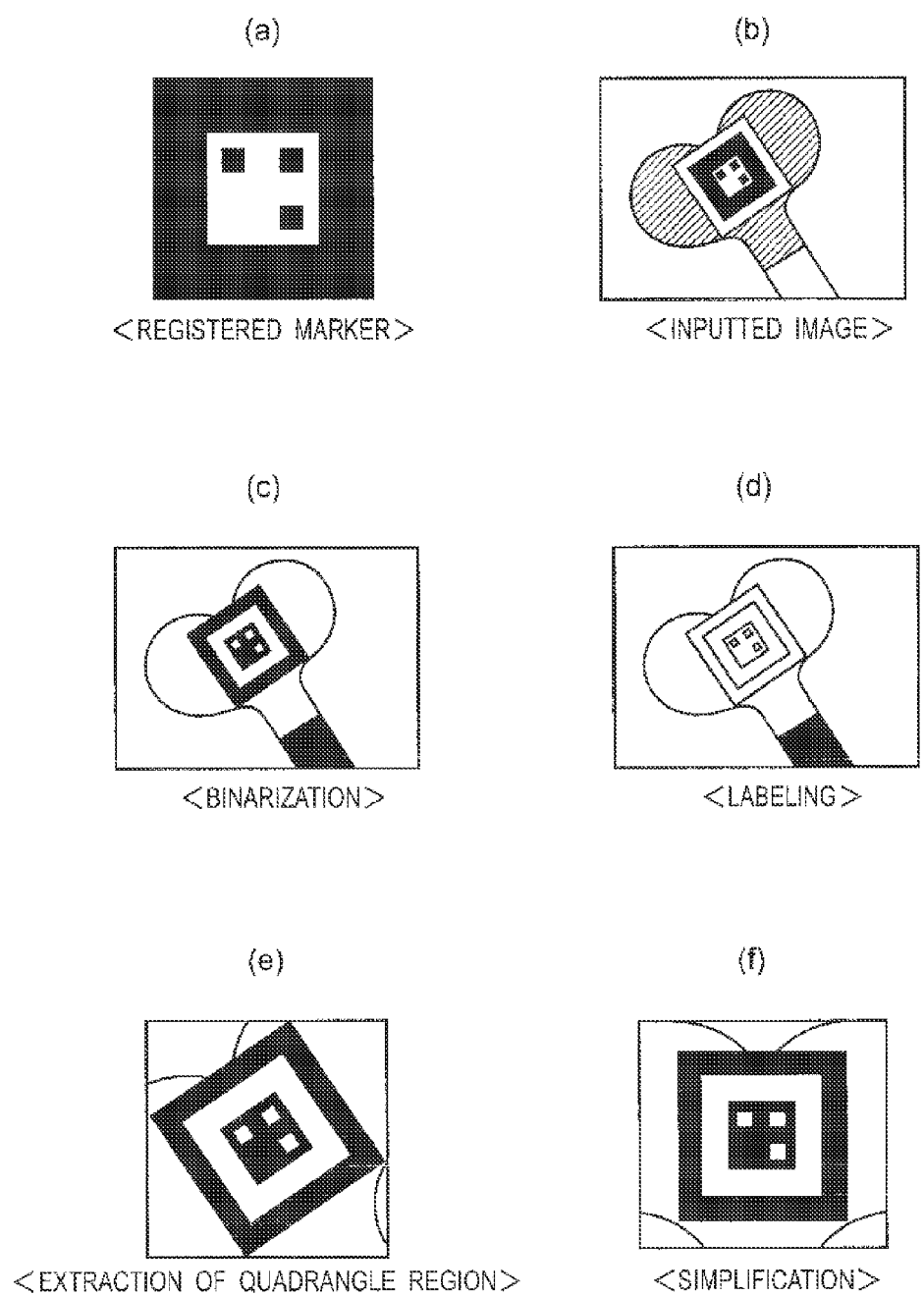
FIG. 10 shows diagrams for explaining a procedure of using a marker provided on a treatment coil used by the apparatus illustrated in FIG. 1 to detect a position and a posture of the coil.

FIG. 10(a) to FIG. 10(f) are a series of explanatory diagrams showing the specific process of the marker recognition. The specific process of the marker recognition when using the marker illustrated in FIG. 10(a) is as follows.

(i) The image from the camera is binarized, and a dark portion in the image is searched.

The image inputted from the camera (FIG. 10(b)) is displayed in a manner that using a threshold value, a region lighter than the threshold value is represented by black and a region darker than the threshold value is represented by white (FIG. 10(c)).

(ii) A closed region in the dark region is searched and labeled.

A closed region in the white region is searched in the binarized image. Further, each closed region is assigned with a number (label) so as to become distinguishable (labeling process). In FIG. 10(d), how the closed regions are distinguished is represented by different colors.

(iii) A number of corners in each closed region is found out, and a region having four corners is determined as a quadrangle.

A number of corners in each closed region are found out, and a region having four corners is determined to be a quadrangle, and taken as a candidate region of the marker (see FIG. 10(e)). At this time, a region whose area of the closed region is very small or very large is excluded.

(iv) An image within the quadrangle is simplified.

By using affine transformation to the quadrangle region, modification is made so that the region becomes square (see FIG. 10(f)).

(v) The simplified image and the registered pattern are compared.

Pixel comparison is performed between the simplified image and the registered marker, and an error is calculated. A region having a smallest error among all the quadrangle regions is determined to be the marker region.

[(IV) Step of Displaying Tracking Result]

In order to operate the transcranial magnetic stimulation apparatus in clinical practice, a user interface is required to notify a user of a part of the brain to which the magnetic flux for the treatment is going to apply stimulation as the result of the head tracking and the coil tracking.

In this embodiment, as a stimulating portion is determined referring to patterns on the brain surface, when the practitioner performs the magnetic stimulation using the treatment coil 33, an interface that displays a three-dimensional model of the brain and allows to freely change the angle and the size of the display is employed.

It is possible to match the current head posture with the three-dimensional model of the brain by using the rigid-body transformation parameters obtained in the initial positional alignment and the rigid-body transformation parameters obtained in the head posture tracking, and to display an expected point for stimulation by the coil 33 on the brain by displaying the converted three-dimensional model of the brain and the tracked position and posture of the treatment coil 33 on the same coordinates.

Figure 14:
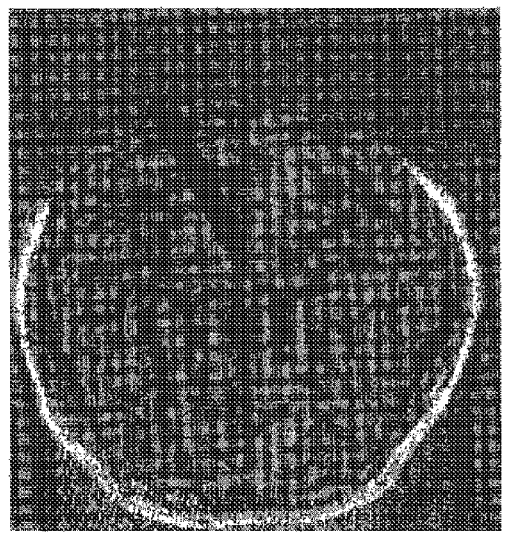
FIG. 14 is, a view illustrating one example of a brain surface displayed by an image displaying means and an image of a magnetic flux generated by the treatment coil of the apparatus illustrated in FIG. 1.

Further, a stimulation point of the treatment coil 33 is represented by a prism through a center of the coil, and the current stimulating region may be determined based on a relation between the prism and the brain surface (see FIG. 14 described later). It can be seen from FIG. 14 that the display is performed such that a relation of a position and an orientation of the magnetic flux for the treatment may be grasped comparative to the three-dimensional MRI image of the brain surface or the head $2h$ of the subject 2.

Practical Example

Next, a specific practical example of the transcranial magnetic stimulation apparatus 1 according to the embodiment of the present invention described above will be explained.

This practical example was achieved using equipment, a development language, and the like as listed in the following table 1.

TABLE 1

| | |
|---|---|
| Projector | Kaga Components Co., Ltd. TAXAN U6-232 Maximal brightness: 2500 lumen Number of pixels of panel: 1024×768 DLP projector |
| Camera | Point Gray Research Dragonfly Express Number of input pixels (in initial positional alignment): 640×480 Number of input pixels (in head tracking): 320×240 |
| PC | OS: Windows XP CPU: Core2 Quad Q6700 2.66 GHz Memory: 3.0 GB |
| Graphic board | Quadro FX 1700 |
| Development language | C++ CUDA |
| Library used | OpenCV ARToolkit Visualization Tool Kit |

[I. Initial Positional Alignment in Practical Example]

As described above, in the initial positional alignment, the initial positions in the MRI data and the stereo measurement data are matched using the ICP algorithm. For this purpose, it is necessary to obtain the three-dimensional data of the face surface used in the ICP from a sectional image obtained by the MRI in advance. Further, as generation of noises during the stereo measurement largely influences the result of the ICP, it is also necessary to reduce noises. Moreover, the correspondence point searching involves very high calculation cost, and requires long time for processing.

Thus, in this practical example, speeding up of the correspondence point searching was achieved by parallelizing the processes employing a development environment called CUDA designed for a GPU (Graphics Processing Unit).

Specifically, the initial positional alignment was performed in the following procedure.

(1) Reading the three-dimensional model of the face obtained from the MRI data.

(2) Projecting random dots to the patient from the projector, and importing the images in a size of 640×480 pixels from the left camera and the right camera.

(3) Performing the face recognition to the left image and the right image, and detecting the face regions in the images. This process was achieved using a function of Open CV.

(4) Performing the edge detection to the left image and the right image using a 3×3 pixel Sobel filter, and performing block matching to 7 pixels around the edge. For the block matching, a block of 11×11 pixel was used. Further, the processes were parallelized using the GPU, and the high speed correspondence point searching was enabled. By detecting edges and searching the correspondence point only around the edges, it is possible to reduce generation of noises due to false correspondence.

(5) Obtaining the three-dimensional position by the triangulation method based on the parallax information obtained by the block matching.

(6) Performing the positional alignment between the measured face shape and the face shape obtained from the MRI data using the ICP algorithm. The ICP algorithm was implemented using a function of a VTK (Visualization Tool Kit), and the rotation matrix R and the parallel translation vector t may be obtained by the execution.

<Three-Dimensional Re-Construction from MRI Image>

Figure 11:
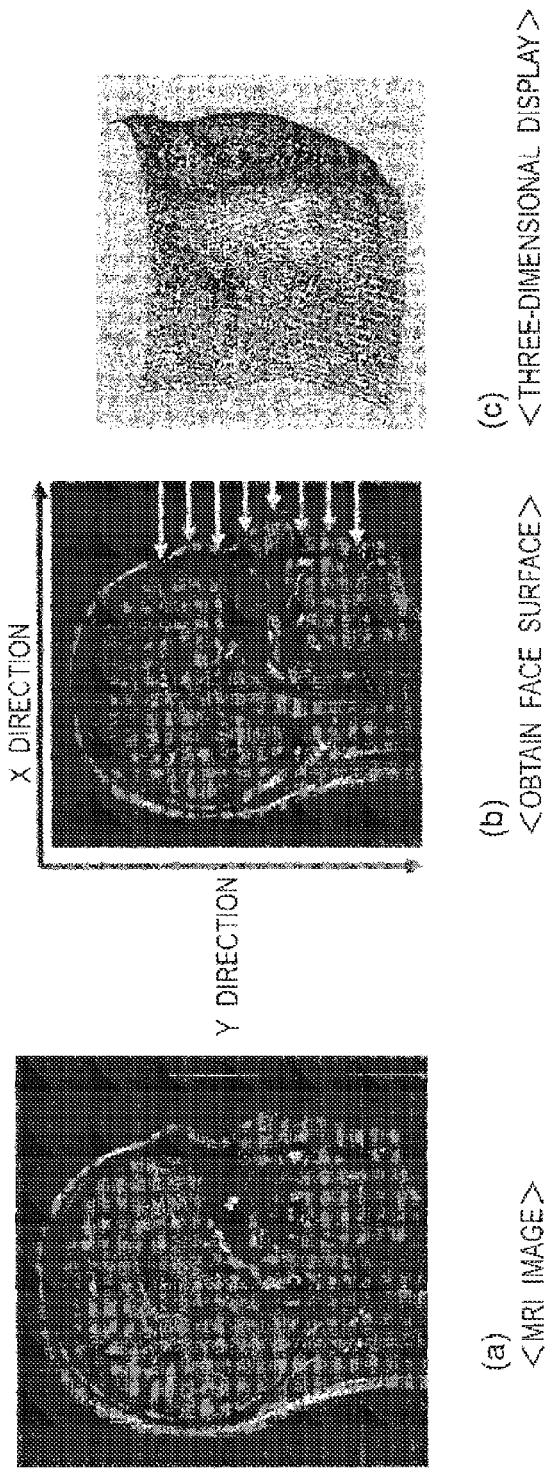
FIG. 11 is a diagram for explaining a procedure, executed by the apparatus illustrated in FIG. 1, of generating a three-dimensional image of the face based on the three-dimensional MRI image of the head.

From the MRI measurement of the subject's head $2h$, it is possible to obtain a result of the head scanning as a set of sectional images as illustrated in FIG. 11(a). In order to perform the positional alignment using the ICP algorithm, it is necessary to obtain a three-dimensional point set of a region (the surface of the face) required for the matching from these sectional images.

The MRI image used in this practical example is configured by 256×256 pixel large, 130 sectional images, for example. A slicing pitch of the sections is 1.40 mm, for example, and a size of a single pixel is 0.98×0.98 mm, for example. Paying attention to the fact that an outline region of the face within the image is indicated in white, as indicated by an arrowed line (11-1) in FIG. 11(b), the scanning is started from a maximum value in the image in the x direction, and a pixel whose brightness value is 30 or higher is first obtained as the surface of the face, for example. Assuming that a number of the sectional image is N ($0 \leq N < 130$) and the obtained pixel value is I(i, j), the obtained pixel may be converted into three-dimensional coordinates $(X, Y, Z)^T$ as in the following expression (Expression 13) using the slicing pitch (e.g., 1.40 mm) and the pixel size (e.g., 0.98×0.98 mm).

$$X=(256-i) \times 0.98$$

$$Y=N \times 1.40$$

$$Z=(256-j) \times 0.98 \quad \text{[Expression 13]}$$

FIG. 11(c) shows a three-dimensional model of the face surface re-constructed from the MRI image. For the point set used in the ICP, only central regions of the face including the characteristic regions of the nose, the eyes, and the mouth are used, instead of the face surface as a whole. The size of the cropped region is empirically determined.

<Noise Reduction Based on Random Dot Pattern Projection>

The correspondence point searching is a most complicated problem in passive stereo measurement. As described above, in the correspondence point searching by the block matching, the correspondence is made between the regions where a difference of the pixel values therebetween within a block is smallest. Accordingly, the correspondence point searching between regions having less characteristic on the surfaces often involves a smaller difference between the pixel values, and thus susceptible to false correspondence.

Therefore, in this practical example, a random dot pattern was projected from the projector, and simulated surface characteristics were added to the measurement object. Further, by detecting the edge (the region including a large color difference in the image) using the 3×3 pixel Sobel filter, and performing the correspondence point searching only to the pixels at the edge and around the edge, generation of noises due to false correspondence was reduced.

Figure 12:
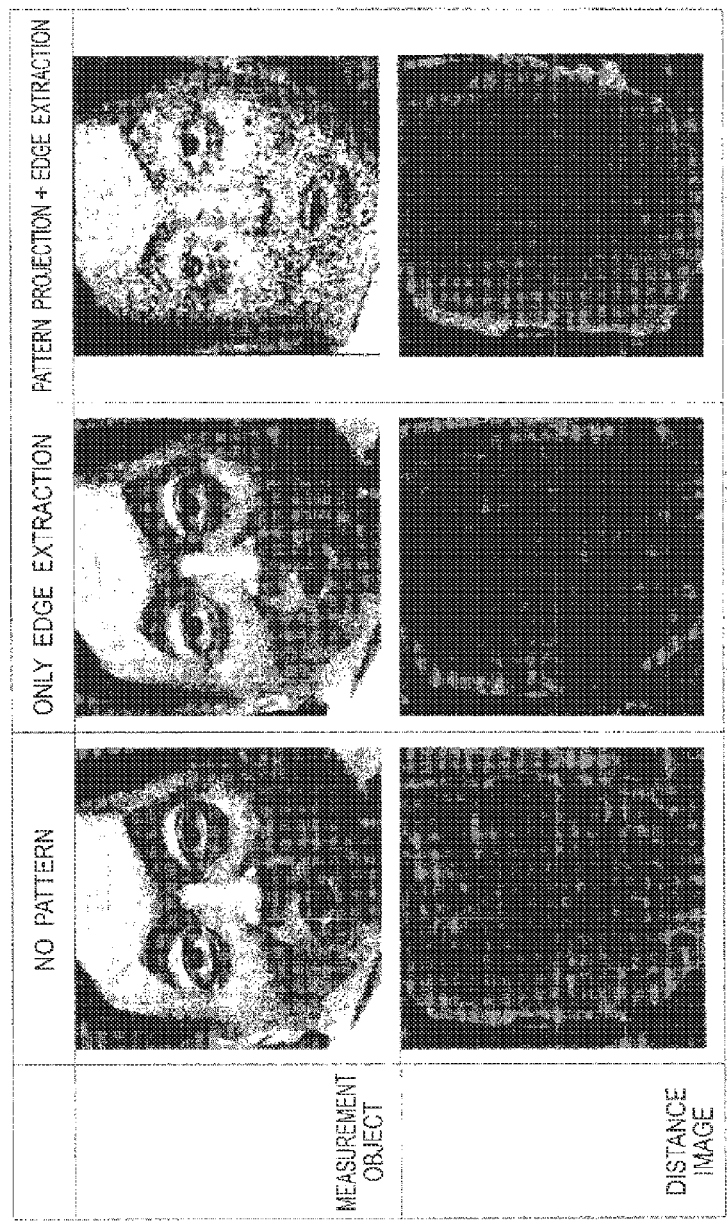
FIG. 12 is a view for explaining a method for accurately detecting a position of the face by projecting a random dot pattern executed by the apparatus illustrated in FIG. 1.

FIG. 12 shows comparison of change of the measurement results of the edge extraction and the pattern projection. The distance images indicate distances from the camera by color variation. It can be seen that when the pattern was not projected and the edge extraction was not performed, the false correspondence occurs as the color variation of the distance image did not match with an object shape. Further, when only the edge extraction was performed, while the distance measurement to the characteristic region in the image was performed, the edges of the region such as the cheek having less color variation was not extracted, and the distance measurement was not performed as a result. Finally, when both the pattern projection and the edge extraction were used, the distance image closely resembling to the face shape was obtained, and it can be seen that the face as a whole was measured while reducing generation of noises as compared to the former examples.

<Speed Up of Correspondence Point Searching Using CUDA>

CUDA is a parallel computing architecture for GPUs developed by NVIDIA Corporation. A GPU has a large number of simple computing units built therein, and exhibits higher computing power than the CPU in highly parallelized computing processing. By using CUDA, it is possible to perform programming for GPUs using the C language. In this practical example, by performing parallel calculation to the correspondence point searching process requiring highest calculation cost and longest time, speeding up and cost reduction of the process was intended (see FIG. 13).

Figure 13:
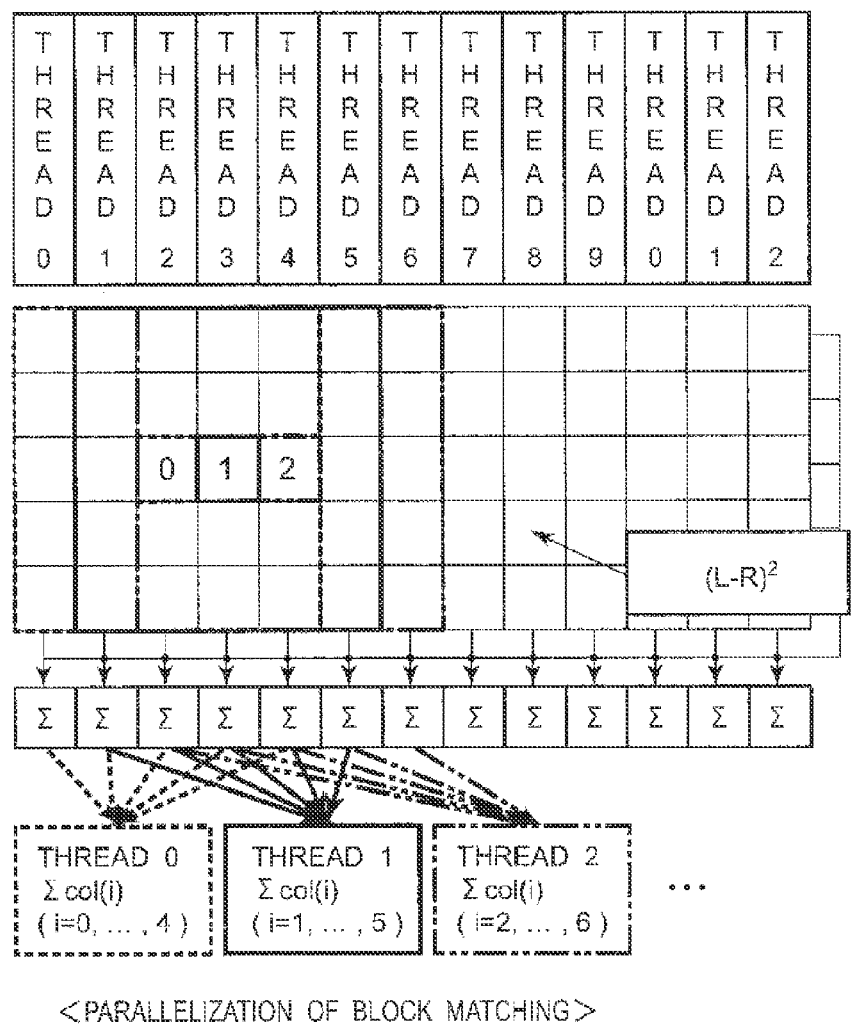
FIG. 13 is a diagram for explaining a block matching parallelization process executed by the apparatus illustrated in FIG. 1.

FIG. 13 exemplifies how 5×5 pixel block matching is performed using 10 threads (THREAD). For each thread, the SSD for one line is calculated and stored. Then, by adding the SSDs stored in the two threads on either side of left and right of the pixel in focus, it is possible to obtain the SSD for the block as a whole.

By fixing the left image, moving the right image pixel by pixel to obtain the SSD, and obtaining a movement amount when the SSD is minimized for each thread, it is possible to obtain the parallax of the images as a whole. In this practical example, the correspondence point searching was performed with block size of 11×11 pixels using 64 threads.

[II. Tracking of Face Posture in Practical Example]

After the initial positional alignment process is completed, tracking of the face posture starts. As described above, in the face posture tracking, the characteristic regions of the face (seven points: the inner and outer corners of both eyes, the corners of the mouth (both ends), and the tip of the nose) are tracked, and a three-dimensional amount of change from the initial state is obtained. In the system according to this practical example, it is necessary to provide the characteristic regions manually. Further, as a precondition, it is required that the initial posture when the tracking starts matches the posture in the initial positional alignment. Specifically, the tracking of the face posture was performed in the following procedure.

(1) Obtaining the images of the initial posture in a size of 240×320 pixels, for example, from the left camera and the right camera.

(2) Obtaining the regions as template images of 17×17 pixel, for example, by clicking the seven points in the inner and outer corners of both eyes, the corners of the mouth (both ends), and the tip of the nose in the right image using a mouse. Further, using the obtained template images, the characteristic regions in the left image are detected by the template matching, and the three-dimensional position of each characteristic region is stored by the stereo view.

(3) Searching the characteristic regions in the images from the left camera and the right camera obtained for each frame, using the template images obtained in the process (2). The three-dimensional positions of the characteristic regions are obtained from the search result by the stereo view.

(4) Obtaining the rigid-body transformation parameters between the three-dimensional position in the initial posture obtained in the process (2) and the three-dimensional position in the current posture obtained in the process (3) by minimizing the error function E in [Expression 2] described above. The steepest descent method is used for this optimization calculation.

[III. Tracking of Treatment Coil in Practical Example]

The position and the posture of the treatment coil are tracked using a known marker. In this practical example, ARToolkit was used for recognizing the marker. ARToolkit is a C language library for realizing augmented reality (AR: Augmented Reality) (Hirokazu Kato, Mark Billinghurst, Koichi Asano, and Keihachiro Tachibana: "An Augmented Reality System and its Calibration based on Marker Tracking"; Transactions of the Virtual Reality Society of Japan, vol. 4, No. 4 (1999)). In this practical example, the marker recognition function of this library was used.

Using the marker illustrated in FIG. 10(a), the four corners of the marker are detected from the left image and the right image. Then, the marker position within the three-dimensional space is obtained by the stereo view. In this practical example, the marker was placed vertically in a central portion of the treatment coil 33. Straight lines from the three-dimensional coordinates of the four corners of the marker passing through a center of the marker and a center of the coil 33 are obtained, and the elongated rectangular shapes are displayed along these lines as the figure corresponding to the magnetic flux irradiated from the treatment coil 33 as illustrated in FIG. 14, and it is possible to grasp the magnetic stimulation point by displaying the rectangular shapes within three-dimensional space along with the brain surface.

[IV. Display of Tracking Result in Practical Example]

<Three-Dimensional Display of Brain>

As described above, the practitioner determines the magnetic stimulating region referring to the pattern of the brain surface of the subject 2. Therefore, it is necessary to generate the three-dimensional model of the brain from the sectional data obtained from the MRI. Therefore, the implementation was performed in the following procedure.

Figure 15:
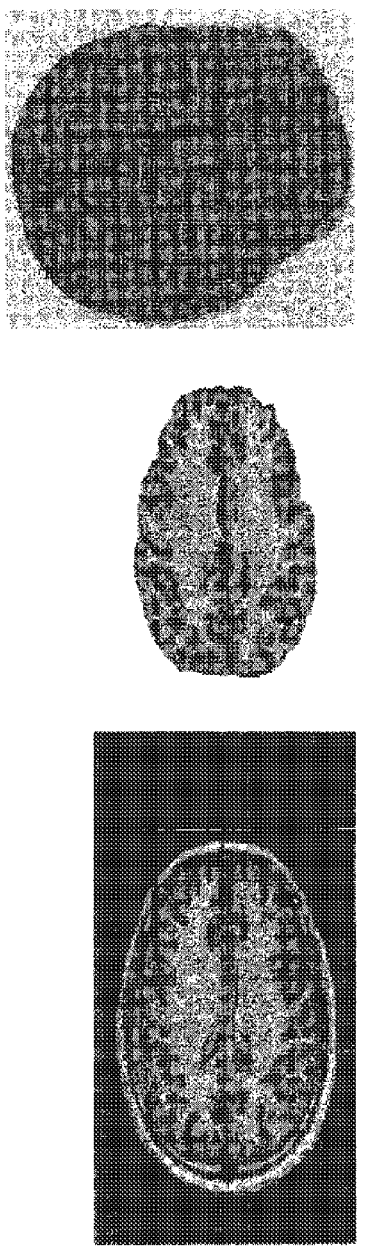
FIG. 15 shows views for explaining three-dimensional display of the brain surface in a practical example using the apparatus illustrated in FIG. 1.

(1) Obtaining the transverse cross-sectional image of the subject's head 2h using software MRIcro (see FIG. 15(a)).

(2) Cropping the image of the brain region manually from the obtained transverse cross-sectional image of the subject's head 2h (see FIG. 15(b)).

(3) Re-constructing the brain image three-dimensionally from the image of the cropped brain region using the three-dimensional re-construction method. With this, the three-dimensional point set of the brain as illustrated in FIG. 15(c) may be obtained.

In the display of the three-dimensional point set of the brain obtained in the process (3), the pattern of the brain surface is often hard to see depending on the display angle. Further, as it is necessary to display an enormous number of points and the calculation cost is very high, this is not suitable for real time display.

Therefore, a mesh model along the brain surface is generated, only the surface is displayed polygonally, and mapping of the brain surface pattern as a texture is performed over the surface. Next, a method of generating the mesh model of the brain and the texture image will be described.

<Generation of Texture Image>

For the generation of the texture image, color information of the three-dimensional point set of the brain is used. Polar coordinates are set taking a center of the brain as an origin, and as illustrated in FIG. 16(a), polar coordinates of each point of the point set data are obtained. For a point expressed by (x, y, z) in the three-dimensional coordinates, an angle (θ, φ) and a distance r of a polar coordinate element are obtained by the following expression (Expression 14).

$$r = \sqrt{x^2 + y^2 + z^2}$$
$$\theta = \cos^{-1} \frac{y}{\sqrt{x^2 + y^2 + z^2}}$$
$$\theta = \cos^{-1} \frac{x}{\sqrt{x^2 + z^2}}$$

[Expression 14]

Figure 17:
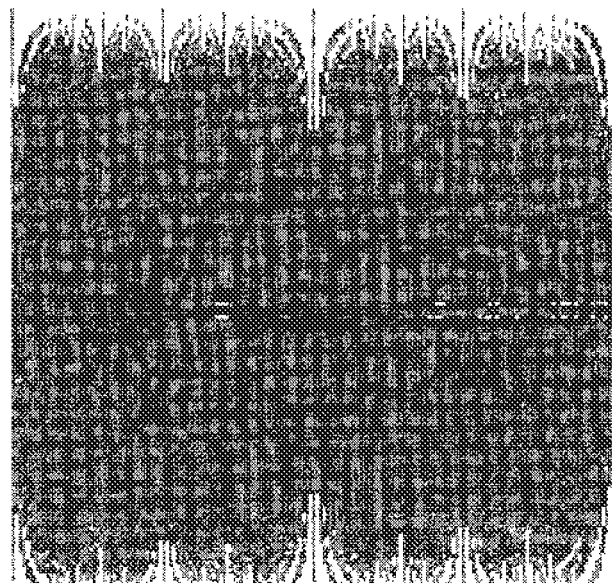
FIG. 17 is a view illustrating one example of the texture image.

Next, an array of 180×180 is prepared, and the number of the row and the number of the line are made correspondent to an angle θ and an angle φ, respectively (see FIG. 16(b)). Grouping is made in a unit of one angle from 0 degree to 180 degrees by one degree to the angle θ and the angle φ, and a point whose distance r is largest among the points included in each group is taken as a brain surface point. The color information of the brain surface point is stored in the array and taken as texture information. The texture image generated from the point set in FIG. 15(c) is illustrated in FIG. 17.

<Generation of Mesh Model>

Figure 18:
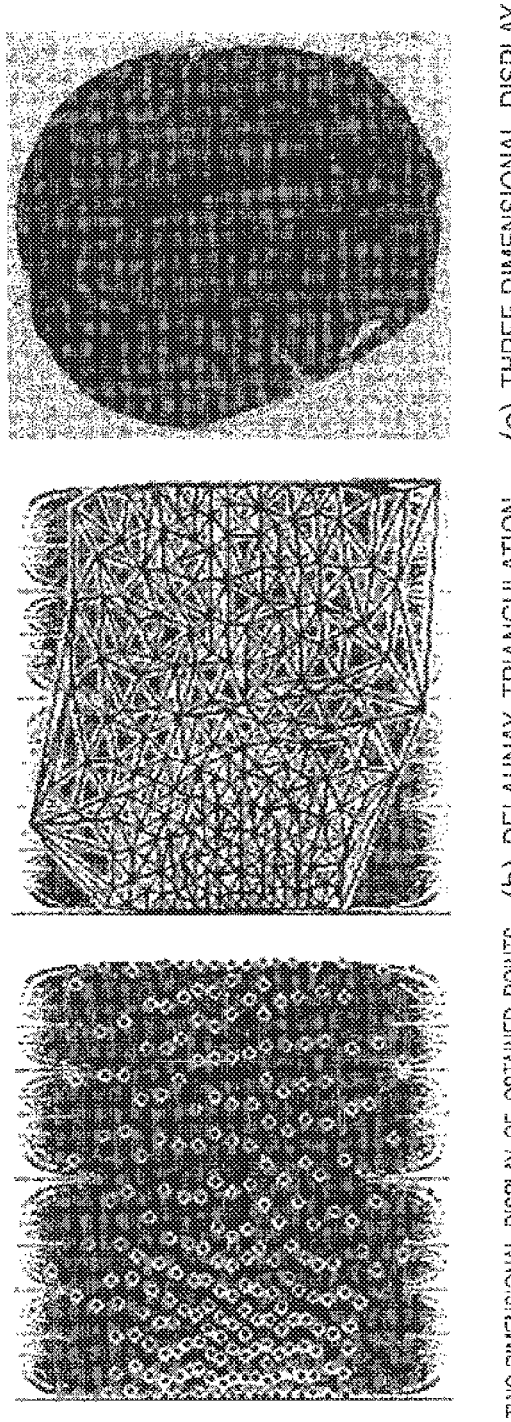
FIG. 18 shows views for explaining generation of a mesh model and a three-dimensional display model in the practical example.

The mesh model is generated based on the sectional image. Borderline coordinates of the brain in the sectional image are obtained, and polar coordinates thereof and three-dimensional coordinates thereof are obtained. An array similar to that used in the generation of the texture image is prepared, and points that have been obtained are stored in the array based on the polar coordinates. With this, as illustrated in FIG. 18(a), it is possible to two-dimensionally map the obtained points. From these points, surface information is obtained using the Delaunay triangulation (Hiroyuki Yamamoto, Shinji Uchiyama, Hideyuki Tamura: "Method for Generating The Delaunay Mesh for Three-Dimensional Modeling", IEICE Transactions D-11, Vol. J83-D-11, No. 5, pp. 745-753 (1995-5)) (see FIG. 18(b)).

Using the surface information and the three-dimensional coordinates thus obtained, the three-dimensional model of the brain surface may be provided. FIG. 18(c) shows the three-dimensionally displayed brain surface on which the texture mapping is performed using the texture image as illustrated in FIG. 17.

[Accuracy Evaluation in Practical Example]

In the above described practical example, accuracy evaluation was performed for each process of "the initial positional alignment", "the tracking of the posture (face posture) of the subject's head", and "the tracking of the treatment coil" described above.

Equipment and such used for the accuracy evaluation was the same as those shown in Table 1. Further, a distance from the stereo camera to the measurement object was set from 70 cm to 100 cm.

<Accuracy Evaluation of "Initial Positional Alignment">

Figure 19:
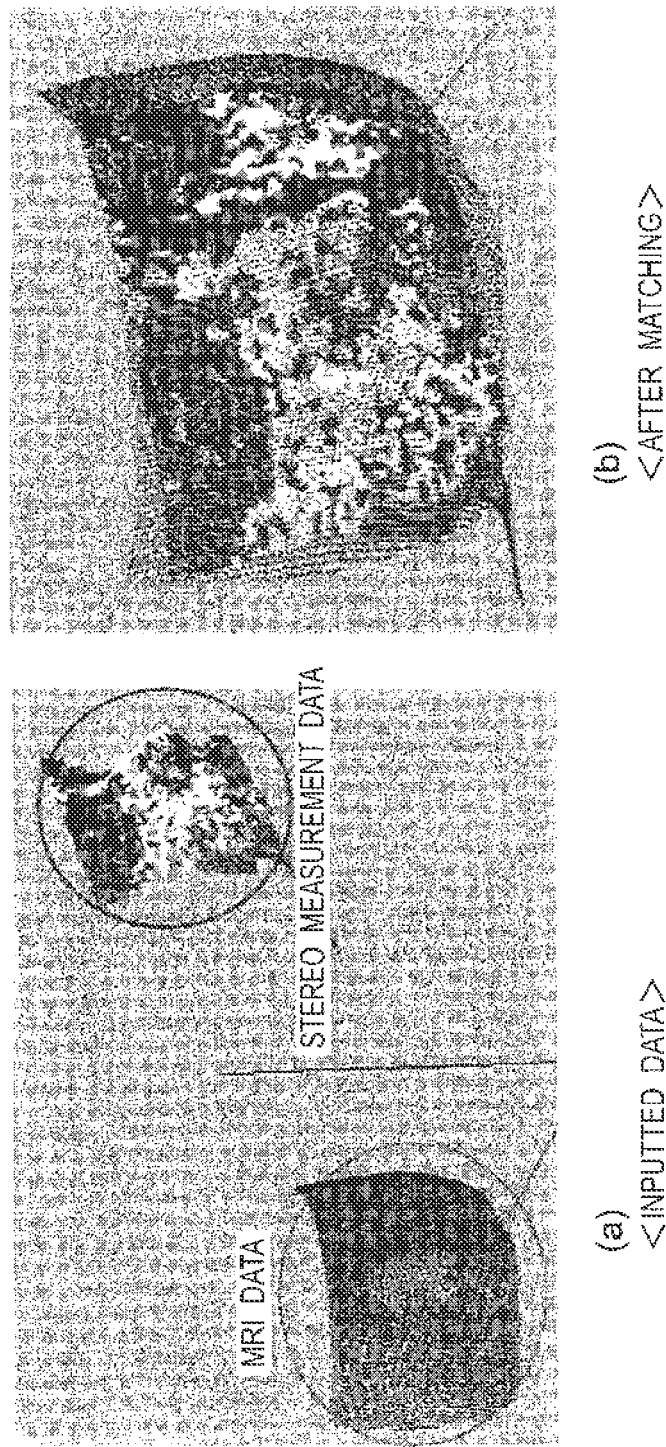
FIG. 19 shows views for explaining accuracy evaluation of an initial positional alignment step in the practical example.

The MRI data and the stereo measurement data as illustrated in FIG. 19(a) were prepared, and the accuracy evaluation of the IPC algorithm described above was performed. Two pieces of data matched using the rigid-body transformation parameters obtained by the IPC algorithm are shown in FIG. 19(b). It can be seen that the two pieces of data are substantially identical by referring to positions of the ridge of the nose and the eyes.

Figure 20:
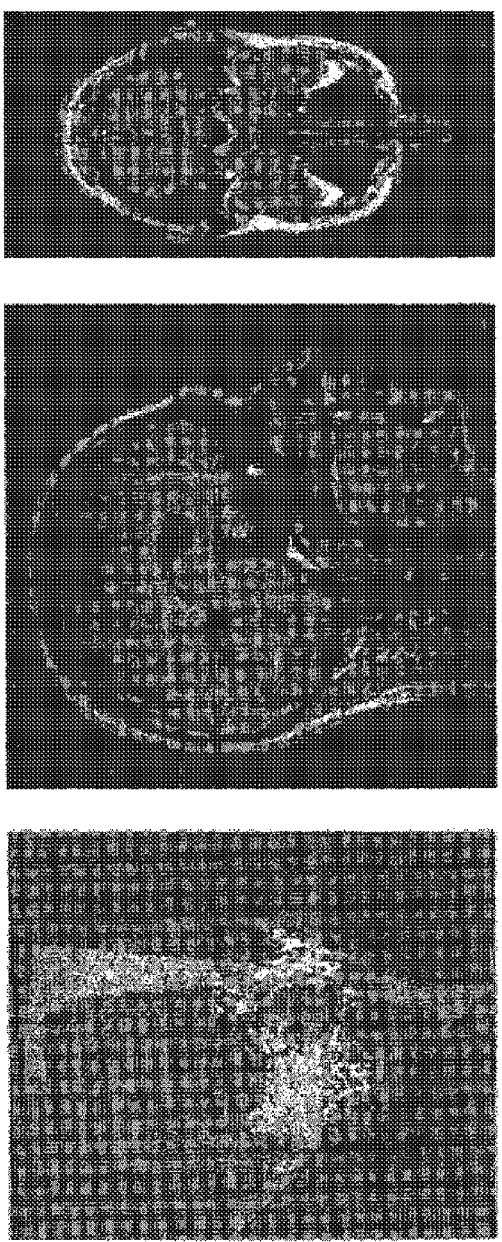
FIG. 20 shows different views for explaining the accuracy evaluation of the initial positional alignment step in the practical example.

FIG. 20 shows the MRI images each superimposed over the stereo measurement data in a state of the initial positional alignment. A longitudinal section and a transverse section obtained along a longitudinal (vertical) plane and a transverse (horizontal) plane shown in FIG. 20(a) are shown in FIG. 20(b) and FIG. 20(c). The stereo measurement data is indicated by a solid curved line over the face surface in FIG. 20(b) and FIG. 20(c). A segment of a line shown right bottom in the figures indicates 1 cm, and it can be seen that the two pieces of data match substantially without error.

<Accuracy Evaluation of "Face Posture Tracking">

Figure 21:
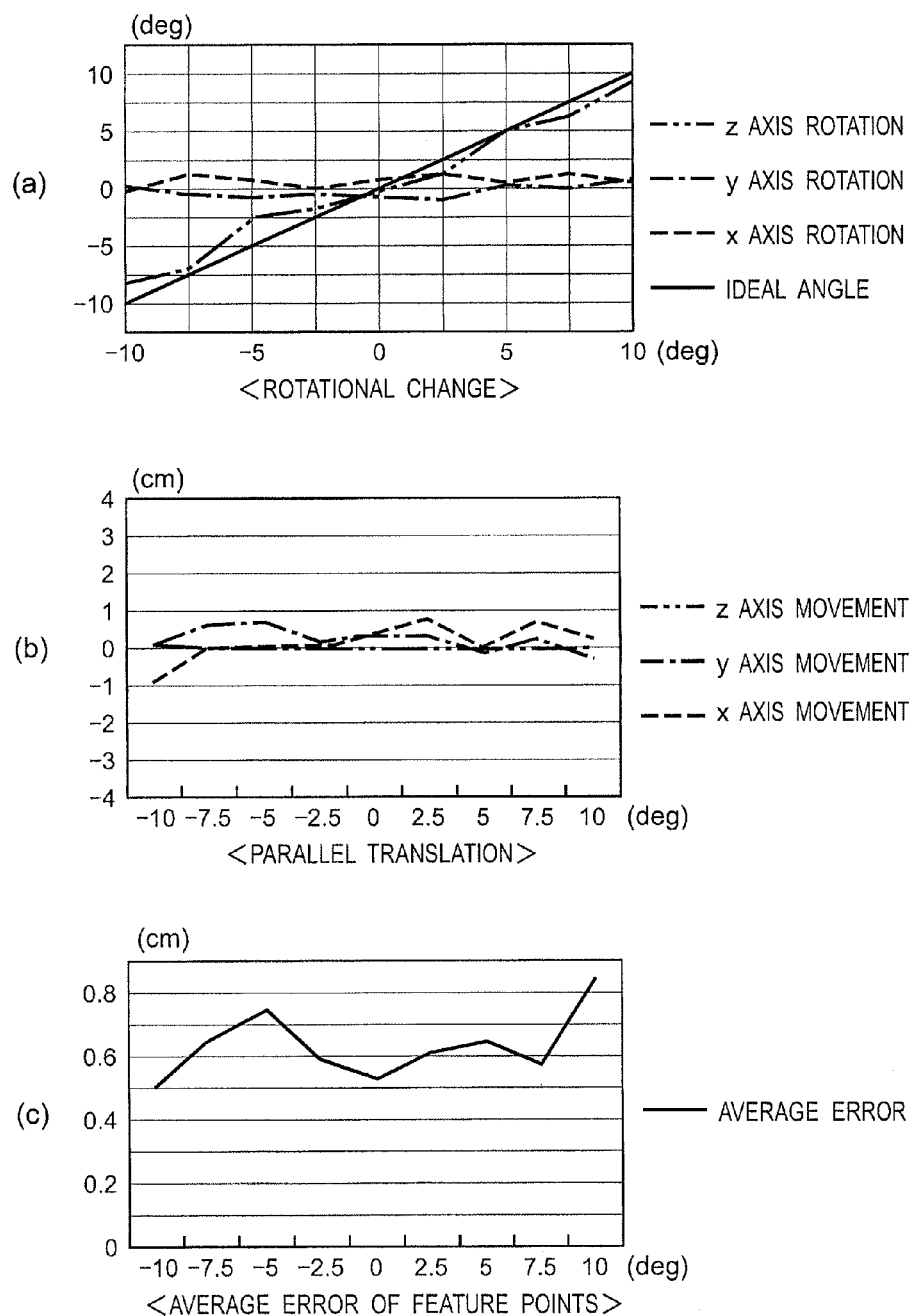
FIG. 21 shows charts for explaining accuracy evaluation of face posture tracking in the practical example.

In the accuracy evaluation of the face posture tracking, a human face model was used, and a rotation matrix, a parallel translation vector, and an average error at each feature point were obtained when this face model is placed on a rotation plate (rotation axis: z axis) and rotated about the z axis by ±12.5 degrees at 2.5-degree intervals. The result is shown in FIG. 21. FIG. 21(a) shows amounts of rotation about the corresponding axes, FIG. 21(b) shows amounts of parallel translation in directions of the corresponding axes, and FIG. 21(c) shows average errors at the corresponding feature points.

As the rotation is provided only about the z axis, as an ideal result, it is desirable that the z axis rotation (indicated by an alternate long and two short dashes line) in the chart of FIG. 21(a) changes as in an ideal line (solid line), and all of the other amounts of change become 0 (zero). It seems from the charts of the rotational change and the parallel translation that the tracking result close to an ideal change was obtained even if including some errors.

Average rotational errors for the corresponding axes were 0.7 degrees about an x axis, 0.5 degrees about a y axis, and 1.1 degrees about the z axis. Further, parallel translational errors in the directions of the corresponding axes were 4 mm along the x axis direction, 3 mm along the y axis direction, and 0 mm along the z axis direction, and an average error between the corresponding feature points and actual measured values was 6 mm.

<Accuracy Evaluation of "Coil Tracking">

In the accuracy evaluation of the coil position tracking, an average error between an observed value at a center of the marker and an actual position within the three-dimensional space was calculated. The average error was 4 mm in the x axis direction, 4 mm in the y axis direction, and 0 mm in the z axis direction, and it was confirmed that the three-dimensional position of the marker was accurately detected.

Here, another practical example included in the present invention, and in particular responding to purposes of a moving operation of moving the magnetic stimulation coil closer to the magnetic stimulating region, and of the positional alignment of the positions of the magnetic stimulation coil and the subject's head with higher accuracy will be described.

Various position detection methods include detection errors, respectively. For example, explaining by a method using the stereo camera 40 in FIG. 1, as the distance from the camera to the photogenic subject is measured by the well known triangulation principle, a theoretical error increases as the distance from the camera to the photogenic subject increases.

In a case in which the transcranial magnetic stimulation apparatus is used at a patient's house (home), instead of a medical facility such as a hospital, medical staff may not be present at the scene of treatment. Accordingly, the patient or the patient's family must, by their own operation, bring an irradiation point of the magnetic stimulation coil close to a sweet spot until the irradiation point comes within a distance range in which the treatment effect is sufficiently provided. If the accuracy required for the treatment in the moving operation may not be obtained, it is necessary to increase the size or the number of turns of the coil to provide a more efficient magnetic stimulation coil, or to increase a current value to be applied to the coil, so as to obtain a required size of the stimulation magnetic field at a desired irradiated site even with some errors.

However, increasing the size of the magnetic stimulation coil or the current value in this manner decreases operability in the coil moving operation performed by the patient, increases the cost of the magnetic stimulation apparatus, and increases power consumption or unwanted radiating electromagnetic waves to environment, possibly resulting in a large obstructive factor when attempting such a magnetic stimulation treatment at home.

On the other hand, the detection method of various positions inevitably includes a theoretical error that cannot be avoided. As described above, for example, when the stereo camera 40 measures positions of two measurement objects including the head 2h of the subject and the magnetic stimulation coil 30, and generates an instructing screen for the patient to perform the operation, such a theoretical error that cannot be avoided is accumulated, and the errors may increase additively as compared to a single positional measurement.

Figure 22:
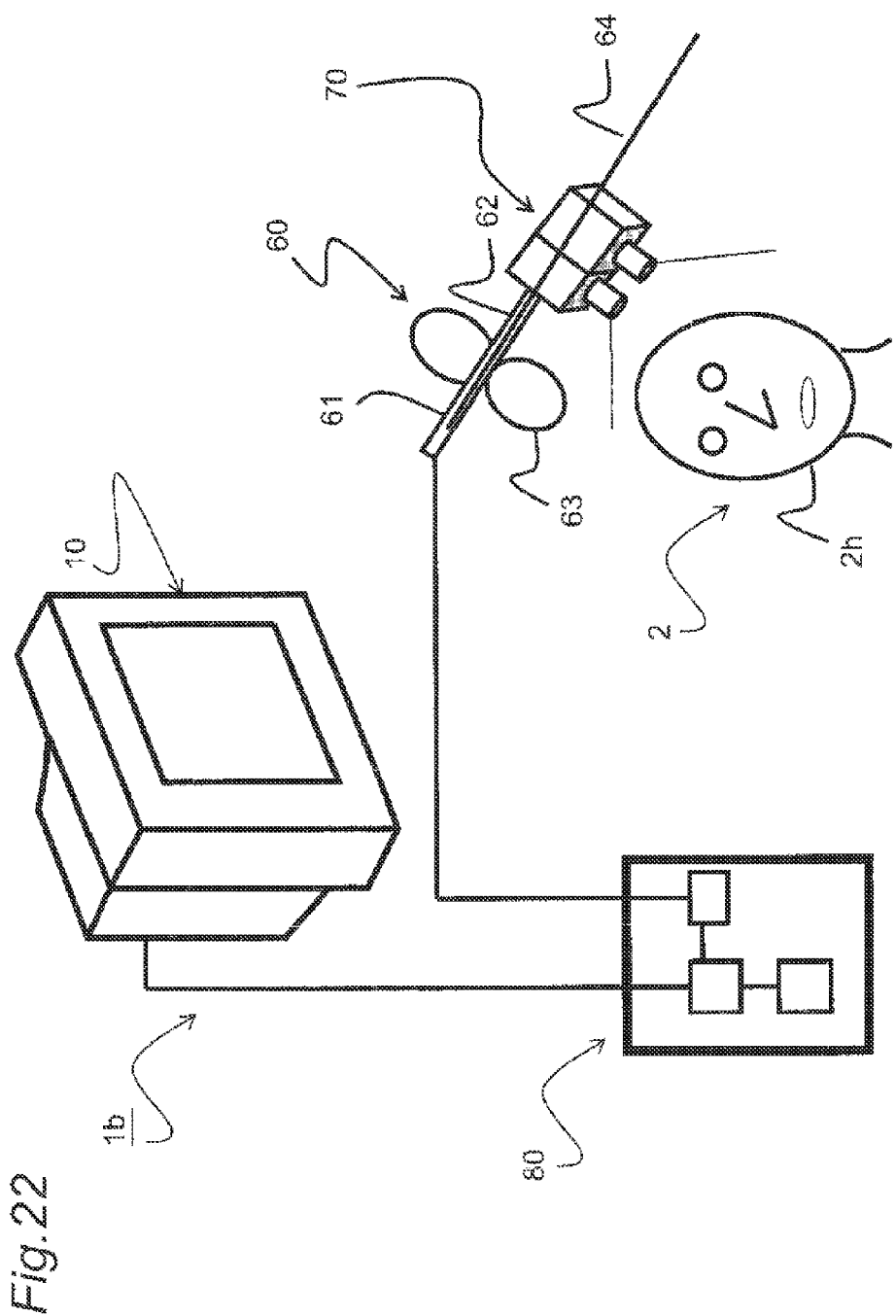
FIG. 22 is a schematic configuration diagram of a transcranial magnetic stimulation apparatus according to a different embodiment of the present invention.

Thus, as illustrated in FIG. 22, in a transcranial magnetic stimulation apparatus 1b according to this embodiment, a stereo camera 70 as a position detection means is configured integrally with a magnetic stimulation coil 60 via a coupling unit 62. As a result, relative differences of the distances and the postures between the magnetic stimulation coil 60 and the stereo camera 70 are constant. It should be appreciated that a configuration different from the above configuration may be employed as long as a mechanism in which the magnetic stimulation coil 60 and the stereo camera 70 are relatively fixed is provided.

Once the position and the posture of the magnetic stimulation coil 60 seen from the measurement coordinate origin of the stereo camera 70 are determined in design or measured at the beginning of use, it is not necessary to perform the measurement thereafter. Accordingly, an object to be measured in the treatment is just the head 2h of the subject 2, and it is possible to ensure to avoid the accumulation of theoretical errors.

It should be noted that in a case in which the stereo camera 70 as an electronic apparatus is provided near the magnetic stimulation coil 60 generating a large magnetic field, the stereo camera 70 may be magnetically shielded with a metal plate if there is a probability that electrical destruction due to a large inductive current generated by the coil 60, or physical or mechanistic destruction associated with magnetic induction is caused. Alternatively, a countermeasure is conceivable that the stereo camera 70 is disposed at a position along a symmetry rotation axis 64 of two volute coils 63 where an inductive magnetic field is theoretically zero because of the structure of the magnetic stimulation coil 60.

Examples of suitable modifications and improvements of this embodiment include the following. For example, a different position detection means may be used in place of the stereo camera 70. Further, when using the stereo camera 70, as its imaging viewpoint is positioned near the magnetic stimulation coil 60 and distant from the viewpoint of the subject 2 who performs the operation, it is possible to provide a screen display easier to see by performing coordinate conversion such that the viewpoint becomes the position of the stereo camera 40 in FIG. 1 described above based on the information of the detected position. Moreover, it is possible to configure such that the image of the subject's head 2h is taken using the second to the fourth example for obtaining the position information within the three-dimensional space such as a monocular camera instead of the stereo camera, and the superimposing over the MRI image of the head or over the image of the head after the movement is performed from the feature points of the shape or in the image such as the outline of the head, the pupils, or the nose bridge.

According to this embodiment including various configurations as described above, utilizing the specific configurations of the various practical examples of the invention previously described, there is provided the transcranial magnetic stimulation apparatus 1b that applies the magnetic stimulation using the magnetic stimulation coil 60 outside the head to a specific portion within the subject's head 2h.

The transcranial magnetic stimulation apparatus 1b is provided with the magnetic stimulation coil 60 configured to change the position and the posture according to the operation, the imaging means 70 such as a stereo camera whose position and posture are fixed relative to the magnetic stimulation coil 60, and a control unit 80 configured to display a screen for instructing of moving operation of the magnetic stimulation coil 60 to the sweet spot.

The control unit 80 records and holds the MRI three-dimensional image of the subject's head, in the image a position of the specific portion to be provided with the magnetic stimulation is marked. And, the control unit 80 superimposes the MRI three-dimensional image of the subject's head and the appearance image of the subject's head taken by the imaging means 70 so that the corresponding portions overlap. Further, the control unit 80 calculates the differences of the distances and the postures between the current appearance image of the current subject's head taken by the imaging means 70 and the appearance image of the subject's head used for the superimposing, where the magnetic stimulation coil 60 is configured such that the patient holds a grip 61 to perform moving operation, and the distance and the posture with respect to the magnetic stimulation coil 60 of the current subject's head may change. Furthermore, by using the result of the calculation, the control unit 80 measures the differences of the distance and the posture between the magnetic stimulation coil 60 and the current sweet spot. Then, the control unit 80 is configured such that using the result of the measurement, a screen for instructing of moving operation of the magnetic stimulation coil 60 to the sweet spot is displayed.

It should be noted that while the above descriptions are related to the transcranial magnetic stimulation treatment for relieving neuropathic pain by providing the magnetic stimulation to the brain nerve by the magnetic stimulation coil provided on the surface of the scalp of the subject (e.g., the patient or the examinee), the present invention is not limited to such a case, and may be effectively used in a different magnetic stimulation application.

As described above, it should be appreciated that the present invention is not limited to the above embodiments, and may be variously modified or improved in design without departing from the scope of the invention.

INDUSTRIAL APPLICABILITY

The present invention provides an image processing method and a transcranial magnetic stimulation apparatus that are capable of irradiating the magnetic flux accurately to a narrow range of irradiation target site when performing the magnetic stimulation treatment especially to the head, and allowing the treatment practitioner to grasp the three-dimensional position of the magnetic stimulation means and the orientation of the magnetic flux in a wide range, and reducing the strain of the patient.

DESCRIPTION OF REFERENCE SYMBOLS 1, 1b TRANSCRANIAL MAGNETIC STIMULATION APPARATUS
2 SUBJECT
2h SUBJECT'S HEAD
10 IMAGE MONITOR UNIT
20 APPARATUS MAIN BODY UNIT
21 IMAGE DISPLAY CONTROL UNIT
22 MAGNETIC STIMULATION COIL CONTROL UNIT
23 THREE-DIMENSIONAL INFORMATION GENERATING UNIT
30, 60 MAGNETIC STIMULATION COIL UNIT
32 MARKER UNIT
33, 63 TREATMENT COIL
40, 70 STEREO CAMERA
41 LEFT CAMERA
42 RIGHT CAMERA
80 CONTROL UNIT

The invention claimed is:

1. A transcranial magnetic stimulation apparatus for applying magnetic stimulation to a specific portion within a patient's head using a magnetic-field generation means disposed outside the head, the apparatus comprising:
the magnetic-field generation means which is capable of moving toward a predetermined treatment irradiation position and posture thereof according to an operation of the patient or a patient assistant;
a storage means which stores a three-dimensional MRI image of a patient's head that has been previously taken;
a three-dimensional appearance image generation means which generates a three-dimensional appearance image of the patient's head in an initial posture;
an image generation means which performs positional alignment between the three-dimensional MRI image and the three-dimensional appearance image, and generates a three-dimensional image of the patient's head after the positional alignment;
a means which stores patterns of face characteristics as templates of characteristic regions, the face characteristics being suitable for tracking and being characteristics in the generated three-dimensional appearance image of the patient's head in the initial posture;
an after-movement image generation means which generates, when the patient's head has been moved, a three-dimensional image of the patient's head after the movement;
a means which finds out characteristic points in a face image after the movement using the templates to obtain three-dimensional coordinates of the characteristic regions;
a means which detects changes of the posture from the initial posture using the characteristic regions in the face image in the initial posture and the characteristic regions in the face image after the movement;
a magnetic-field generation means image generation means which generates an image of the magnetic-field generation means that indicates a current position of the magnetic-field generation means operated so as to maintain a positional relation with a specific portion on the three-dimensional MRI image of the patient's head;
a display means which displays the three-dimensional image of the patient's head after the movement and the image of the magnetic-field generation means in one image; and
a means which stores position and posture information about the predetermined treatment irradiation position and posture of the magnetic-field generating means as target information, in relation to the three-dimensional image of the patient's head after the movement,
wherein the predetermined treatment irradiation position and posture of the magnetic-field generating means is indicated as a target on the display means, and wherein the means which stores patterns of face characteristics as templates of characteristic regions is configured to store the patterns of face characteristics as templates of characteristic regions without using any laser projectors.

2. The transcranial magnetic stimulation apparatus according to claim 1, wherein
the image generation means includes:
a selection means which selects points $m_i$ satisfying a predetermined condition from a plurality of points $b_j$ included in the three-dimensional appearance image, the points $m_i$ being selected respectively for N points $a_i$ included in the three-dimensional MRI image;
a parameter determining means which determines, at each of the points $m_i$ selected by the selection means, a rotation matrix R and a parallel translation vector t as parameters for performing rigid-body transformation such that a value of an error function $E(R, t)$ is minimized, the rigid-body transformation converting the points included in the three-dimensional MRI image into the corresponding points included in the three-dimensional appearance image, the error function $E(R, t)$ being configured by a predetermined calculation procedure using the rotation matrix R and the parallel translation vector t; and
a data processing means which performs the rigid-body transformation to each of the points $a_i$ using the rotation matrix R and the parallel translation vector t until the value of the error function $E(R, t)$ becomes equal to or smaller than a predetermined threshold value, and to cause the selection means to select the points $m_i$ respectively, for the points $a_i$ after the conversion, and the parameter determining means to determine the rotation matrix R and the parallel translation vector t.

3. The transcranial magnetic stimulation apparatus according to claim 2, wherein
the selection means selects the points $m_i$ having a smallest Euclidean distance from the plurality of points $b_j$, the points $m_i$ being selected respectively for the N points $a_i$.

4. The transcranial magnetic stimulation apparatus according to claim 2, wherein the error function $E(R, t)$ satisfies (Expression 3)

$$E(R, t) = \sum_{i=1}^{N} |Ra_i + t - m_i|.$$ [Expression 3]

5. A transcranial magnetic stimulation apparatus for applying magnetic stimulation to a specific portion within a subject's head using a magnetic-field generation means disposed outside the head, the apparatus comprising:
- an image data processing device which tracks a position and an orientation of a subject's head, wherein the image data processing device includes:
  - an image generation means which generates a three-dimensional appearance image of the subject's head in an initial posture;
  - an extraction and storage means which extracts at least one characteristic region from the three-dimensional appearance image to store as a three-dimensional template image;
  - a means which stores patterns of face characteristics as templates of the characteristic region without using any laser projectors, the face characteristics being suitable for tracking and being characteristics in the generated three-dimensional appearance image of the subject's head in the initial posture;
  - an after-movement image generation means which generates, when the subject's head has been moved, a three-dimensional appearance image of the subject's head after the movement;
  - a means which finds out characteristic points in a face image after the movement using the templates to obtain three-dimensional coordinates of the characteristic region;
  - a means which detects changes of the posture from the initial posture using the characteristic region in the face image in the initial posture and the characteristic regions in the face image after the movement;
  - a characteristic region determination means which moves the template image over the three-dimensional image of the subject's head after the movement, and determines a position at which correlation between the both image data is maximized as a position of the characteristic region after the movement; and
  - a parameter determining means which determines a rotation matrix R and a parallel translation vector t as parameters for performing rigid-body transformation such that a value of an error function E(R, t) is minimized, the rigid-body transformation converting points included in the characteristic region before the movement into the corresponding points included in the characteristic region after the movement, the error function E(R, t) being configured by a predetermined calculation procedure using the rotation matrix R and the parallel translation vector t.

6. The transcranial magnetic stimulation apparatus according to claim 5, wherein the error function E(R, t) satisfies (Expression 4)

$$E = \sum_{i=0}^{N-1} w_i (Rx_i + t - y_i)^T (Rx_i + t - y_i)$$ [Expression 4]

where N is a number equal to or greater than two representing a number of feature points included in the characteristic region, $x_i$ represents a three-dimensional position of each of the feature points included in the characteristic region of the three-dimensional image of the subject's head before the movement of the subject's head, $y_i$ represents a three-dimensional position of each of the feature points included in the characteristic region of the three-dimensional subject's head image after the movement of the subject's head, and $w_i$ represents a weighting coefficient of each of the feature points.

7. The transcranial magnetic stimulation apparatus according to claim 1, wherein the three-dimensional appearance image of the patient's head is generated as a three-dimensional image using parallax between images taken from a plurality of viewpoints.

8. The transcranial magnetic stimulation apparatus according to claim 1, wherein the three-dimensional appearance image of the patient's head is generated using a time by which one of light and an ultrasonic wave arrives from one viewpoint.

9. The transcranial magnetic stimulation apparatus according to claim 1, wherein a position and a posture of an imaging means of the three-dimensional appearance image generation means is fixed with respect to the operational object, the imaging means being capable of taking an image of the patient's head.

10. The transcranial magnetic stimulation apparatus according to claim 2, wherein the three-dimensional appearance image of the patient's head is generated as a three-dimensional image using parallax between images taken from a plurality of viewpoints.

11. The transcranial magnetic stimulation apparatus according to claim 5, wherein the three-dimensional appearance image of the subject's head is generated as a three-dimensional image using parallax between images taken from a plurality of viewpoints.

12. The transcranial magnetic stimulation apparatus according to claim 2, wherein
- the three-dimensional appearance image of the patient's head is generated using a time by which one of light and an ultrasonic wave arrives from one viewpoint.

13. The transcranial magnetic stimulation apparatus according to claim 5, wherein
- the three-dimensional appearance image of the subject's head is generated using a time by which one of light and an ultrasonic wave arrives from one viewpoint.

14. The transcranial magnetic stimulation apparatus according to claim 2, wherein
- a position and a posture of an imaging means of the three-dimensional appearance image generation means is fixed with respect to the operational object, the imaging means being capable of taking an image of the patient's head.

15. The transcranial magnetic stimulation apparatus according to claim 5, wherein
- a position and a posture of an imaging means of the three-dimensional appearance image generation means is fixed with respect to the operational object, the imaging means being capable of taking an image of the subject's head.

16. The transcranial magnetic stimulation apparatus according to claim 1, wherein
- the means which stores patterns of face characteristics as templates of characteristic regions is configured to store the patterns of face characteristics as templates of characteristic regions in response to a user identifying the patterns of face characteristics in the generated three-dimensional appearance image of the patient's head in the initial posture.

17. The transcranial magnetic stimulation apparatus according to claim 1, wherein the characteristic regions comprise inner and outer corners of both of the patient's eyes.

18. The transcranial magnetic stimulation apparatus according to claim 1, wherein the characteristic regions comprise corners of the patient's mouth.

19. The transcranial magnetic stimulation apparatus according to claim 1, wherein the patterns of face characteristics stored as templates of characteristic regions comprise variations in brightness of the patient's face.

20. The transcranial magnetic stimulation apparatus according to claim 1, wherein the patterns of face characteristics stored as templates of characteristic regions comprise variations in color of the patient's face.

21. A transcranial magnetic stimulation apparatus for applying magnetic stimulation to a specific portion within a patient's head using a magnetic-field generation means disposed outside the head, the apparatus comprising:

the magnetic-field generation means which is capable of moving toward a predetermined treatment irradiation position and posture thereof according to an operation of the patient or a patient assistant;

a storage means which stores a three-dimensional MRI image of a patient's head that has been previously taken;

a three-dimensional appearance image generation means which generates a three-dimensional appearance image of the patient's head in an initial posture;

an image generation means which performs positional alignment between the three-dimensional MRI image and the three-dimensional appearance image, and generates a three-dimensional image of the patient's head after the positional alignment;

a means which stores patterns of face characteristics as templates of characteristic regions, the face characteristics being suitable for tracking and being characteristics in the generated three-dimensional appearance image of the patient's head in the initial posture;

an after-movement image generation means which generates, when the patient's head has been moved, a three-dimensional image of the patient's head after the movement;

a means which finds out characteristic points in a face image after the movement using the templates to obtain three-dimensional coordinates of the characteristic regions;

a means which detects changes of the posture from the initial posture using the characteristic regions in the face image in the initial posture and the characteristic regions in the face image after the movement;

a magnetic-field generation means image generation means which generates an image of the magnetic-field generation means that indicates a current position of the magnetic-field generation means operated so as to maintain a positional relation with a specific portion on the three-dimensional MRI image of the patient's head;

a display means which displays the three-dimensional image of the patient's head after the movement and the image of the magnetic-field generation means in one image; and a means which stores position and posture information about the predetermined treatment irradiation position and posture of the magnetic-field generating means as target information, in relation to the three-dimensional image of the patient's head after the movement, wherein the predetermined treatment irradiation position and posture of the magnetic-field generating means is indicated as a target on the display means, and wherein the means which stores patterns of face characteristics as templates of characteristic regions is configured to store the patterns of face characteristics as templates of characteristic regions without using any reflective markers affixed to the patient.

22. A transcranial magnetic stimulation apparatus for applying magnetic stimulation to a specific portion within a subject's head using a magnetic-field generation means disposed outside the head, the apparatus comprising:

an image data processing device which tracks a position and an orientation of a subject's head, wherein the image data processing device includes:

an image generation means which generates a three-dimensional appearance image of the subject's head in an initial posture;

an extraction and storage means which extracts at least one characteristic region from the three-dimensional appearance image to store as a three-dimensional template image;

a means which stores patterns of face characteristics as templates of the characteristic region without using any reflective markers affixed to the subject, the face characteristics being suitable for tracking and being characteristics in the generated three-dimensional appearance image of the subject's head in the initial posture;

an after-movement image generation means which generates, when the subject's head has been moved, a three-dimensional appearance image of the subject's head after the movement;

a means which finds out characteristic points in a face image after the movement using the templates to obtain three-dimensional coordinates of the characteristic region;

a means which detects changes of the posture from the initial posture using the characteristic region in the face image in the initial posture and the characteristic regions in the face image after the movement;

a characteristic region determination means which moves the template image over the three-dimensional image of the subject's head after the movement, and determines a position at which correlation between the both image data is maximized as a position of the characteristic region after the movement; and a parameter determining means which determines a rotation matrix R and a parallel translation vector t as parameters for performing rigid-body transformation such that a value of an error function $E(R, t)$ is minimized, the rigid-body transformation converting points included in the characteristic region before the movement into the corresponding points included in the characteristic region after the movement, the error function $E(R, t)$ being configured by a predetermined calculation procedure using the rotation matrix R and the parallel translation vector t.

\* \* \* \* \*